United States Patent
Hill et al.

(10) Patent No.: US 9,908,928 B2
(45) Date of Patent: *Mar. 6, 2018

(54) ARTIFICIAL SIGNAL PEPTIDE

(71) Applicant: APOGENIX AG, Heidelberg (DE)

(72) Inventors: Oliver Hill, Neckarsteinach (DE); Christian Gieffers, Dossenheim (DE); Meinolf Thiemann, Schriesheim (DE)

(73) Assignee: Apogenix AG, Heidelberg (DE)

( * ) Notice: Subject to any disclaimer, the term of this patent is extended or adjusted under 35 U.S.C. 154(b) by 0 days.

This patent is subject to a terminal disclaimer.

(21) Appl. No.: 15/239,127

(22) Filed: Aug. 17, 2016

(65) Prior Publication Data

US 2016/0362471 A1 Dec. 15, 2016

Related U.S. Application Data

(62) Division of application No. 14/415,871, filed as application No. PCT/EP2013/065248 on Jul. 18, 2013, now Pat. No. 9,434,783.

(30) Foreign Application Priority Data

Jul. 18, 2012 (EP) .................................. 12176978
Jul. 18, 2012 (EP) .................................. 12176980

(51) Int. Cl.
*C07K 14/705* (2006.01)
*C07K 7/08* (2006.01)
*C07K 16/00* (2006.01)
*C07K 14/525* (2006.01)
*C07K 16/18* (2006.01)
*A61K 38/17* (2006.01)
*A61K 39/395* (2006.01)

(52) U.S. Cl.
CPC .... *C07K 14/70578* (2013.01); *A61K 38/1793* (2013.01); *A61K 39/3955* (2013.01); *C07K 7/08* (2013.01); *C07K 14/525* (2013.01); *C07K 16/00* (2013.01); *C07K 16/18* (2013.01); *C07K 2316/52* (2013.01); *C07K 2317/524* (2013.01); *C07K 2317/526* (2013.01); *C07K 2319/00* (2013.01); *C07K 2319/02* (2013.01); *C07K 2319/30* (2013.01); *C07K 2319/74* (2013.01)

(58) Field of Classification Search
CPC ............ C07K 14/525; C07K 14/70578; C07K 16/00; C07K 16/18; C07K 7/08; C07K 2319/00; C07K 2319/02; C07K 2319/30; C07K 2319/74; C07K 2316/52; C07K 2317/524; C07K 2317/526; A61K 39/3955; A61K 38/1793
See application file for complete search history.

(56) References Cited

U.S. PATENT DOCUMENTS 6,306,395 B1  10/2001  Nakamura et al.

FOREIGN PATENT DOCUMENTS

| CN | 102497886 A | 6/2012 |
| WO | 98/38304 A1 | 9/1998 |
| WO | 2004/085478 A2 | 10/2004 |
| WO | 2008/080623 A2 | 7/2008 |

OTHER PUBLICATIONS

International Search Report cited in PCT/EP2013/065248 dated Oct. 14, 2013.
Minihane BJ and Brown DE. Biotechnology Advances. 4(2):207-218. 1986. Available online at—doi:10.1016/0734-9750(86)90309-5.
Tuettenberg et al., "Pharmacokinetics, pharmacodynamics safety and tolerability of APG101, a CD95-Fc fusion protein, in healthy volunteers and two glioma patients", Intl. Immunopharm., vol. 13, Mar. 21, 2012, pp. 93-100.

*Primary Examiner* — Robert S Landsman
(74) *Attorney, Agent, or Firm* — Perkins Coie LLP; Viola T. Kung

(57) ABSTRACT

The present invention relates to an isolated fusion protein comprising an extracellular CD95 domain or a functional fragment thereof and an Fc domain or functional fragment thereof, formulations providing such fusion protein in a stable form as well as a method for producing such a fusion protein.

6 Claims, 9 Drawing Sheets

Downstream process known from prior art

Inventive downstream process

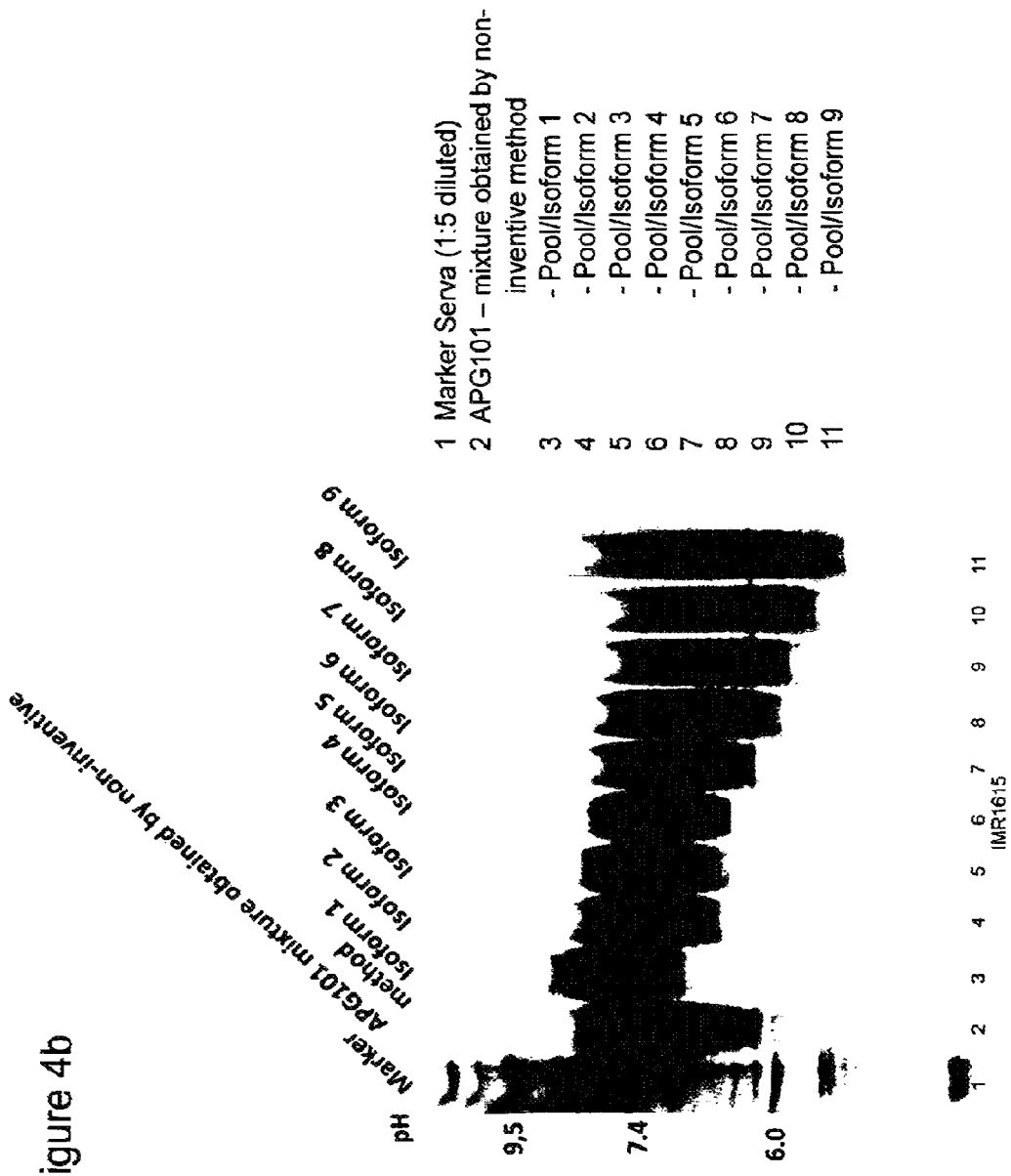

SEQUENCE LISTING

```
<160> NUMBER OF SEQ ID NOS: 19

<210> SEQ ID NO 1
<211> LENGTH: 400
<212> TYPE: PRT
<213> ORGANISM: Artificial Sequence
<220> FEATURE:
<223> OTHER INFORMATION: Recombinant fusion protein consisting of human
      CD95 extracellular domain with human IgG1 FC-part to its C-
      terminus
<220> FEATURE:
<221> NAME/KEY: SIGNAL
<222> LOCATION: (1)..(16)
<223> OTHER INFORMATION: Variable cleavage sites
<220> FEATURE:
<221> NAME/KEY: SIGNAL
<222> LOCATION: (1)..(20)
<223> OTHER INFORMATION: Variable cleavage sites
<220> FEATURE:
<221> NAME/KEY: SIGNAL
<222> LOCATION: (1)..(25)
<223> OTHER INFORMATION: Variable cleavage sites
<220> FEATURE:
<221> NAME/KEY: DOMAIN
<222> LOCATION: (26)..(172)
<223> OTHER INFORMATION: Human CD95 extracellular domain
<220> FEATURE:
<221> NAME/KEY: MOD_RES
<222> LOCATION: (26)..(26)
<223> OTHER INFORMATION: PYRROLIDONE CARBOXYLIC ACID
<220> FEATURE:
<221> NAME/KEY: DISULFID
<222> LOCATION: (59)..(73)
<220> FEATURE:
<221> NAME/KEY: DISULFID
<222> LOCATION: (63)..(82)
<220> FEATURE:
<221> NAME/KEY: DISULFID
<222> LOCATION: (85)..(101)
<220> FEATURE:
<221> NAME/KEY: DISULFID
<222> LOCATION: (104)..(119)
<220> FEATURE:
<221> NAME/KEY: DISULFID
<222> LOCATION: (107)..(127)
<220> FEATURE:
<221> NAME/KEY: CARBOHYD
<222> LOCATION: (118)..(118)
<223> OTHER INFORMATION: N-linked Glycosylation at Position N118
<220> FEATURE:
<221> NAME/KEY: DISULFID
<222> LOCATION: (129)..(143)
```

```
<220> FEATURE:
<221> NAME/KEY: DISULFID
<222> LOCATION: (135)..(140)
<220> FEATURE:
<221> NAME/KEY: CARBOHYD
<222> LOCATION: (136)..(136)
<223> OTHER INFORMATION: N-linked Glycosylation at Position N136
<220> FEATURE:
<221> NAME/KEY: DISULFID
<222> LOCATION: (146)..(157)
<220> FEATURE:
<221> NAME/KEY: DISULFID
<222> LOCATION: (149)..(165)
<220> FEATURE:
<221> NAME/KEY: DOMAIN
<222> LOCATION: (172)..(400)
<223> OTHER INFORMATION: Human IgG1-FC domain (one amino acid overlap
      with CD95 domain)
<220> FEATURE:
<221> NAME/KEY: DISULFID
<222> LOCATION: (173)..(173)
<223> OTHER INFORMATION: Interchain cystine forming residue.
<220> FEATURE:
<221> NAME/KEY: DISULFID
<222> LOCATION: (179)..(179)
<223> OTHER INFORMATION: Interchain cystine forming residue.
<220> FEATURE:
<221> NAME/KEY: DISULFID
<222> LOCATION: (182)..(182)
<223> OTHER INFORMATION: Interchain cystine forming residue
<220> FEATURE:
<221> NAME/KEY: DISULFID
<222> LOCATION: (214)..(274)
<220> FEATURE:
<221> NAME/KEY: CARBOHYD
<222> LOCATION: (250)..(250)
<223> OTHER INFORMATION: N-linked Glycosylation at Position N250
<220> FEATURE:
<221> NAME/KEY: DISULFID
<222> LOCATION: (320)..(378)

<400> SEQUENCE: 1

Met Val Gly Ile Trp Thr Leu Leu Pro Leu Val Leu Thr Ser Val Ala
1               5                   10                  15

Arg Leu Ser Ser Lys Ser Val Asn Ala Gln Val Thr Asp Ile Asn Ser
                20                  25                  30

Lys Gly Leu Glu Leu Arg Lys Thr Val Thr Thr Val Glu Thr Gln Asn
            35                  40                  45

Leu Glu Gly Leu His His Asp Gly Gln Phe Cys His Lys Pro Cys Pro
    50                  55                  60

Pro Gly Glu Arg Lys Ala Arg Asp Cys Thr Val Asn Gly Asp Glu Pro
65                  70                  75                  80

Asp Cys Val Pro Cys Gln Glu Gly Lys Glu Tyr Thr Asp Lys Ala His
                85                  90                  95

Phe Ser Ser Lys Cys Arg Arg Cys Arg Leu Cys Asp Glu Gly His Gly
            100                 105                 110

Leu Glu Val Glu Ile Asn Cys Thr Arg Thr Gln Asn Thr Lys Cys Arg
        115                 120                 125

Cys Lys Pro Asn Phe Phe Cys Asn Ser Thr Val Cys Glu His Cys Asp
130                 135                 140

Pro Cys Thr Lys Cys Glu His Gly Ile Ile Lys Glu Cys Thr Leu Thr
145                 150                 155                 160

Ser Asn Thr Lys Cys Lys Glu Glu Gly Ser Arg Ser Cys Asp Lys Thr
                165                 170                 175

His Thr Cys Pro Pro Cys Pro Ala Pro Glu Leu Leu Gly Gly Pro Ser
            180                 185                 190
```

```
Val Phe Leu Phe Pro Pro Lys Pro Lys Asp Thr Leu Met Ile Ser Arg
        195                 200                 205

Thr Pro Glu Val Thr Cys Val Val Val Asp Val Ser His Glu Asp Pro
    210                 215                 220

Glu Val Lys Phe Asn Trp Tyr Val Asp Gly Val Glu Val His Asn Ala
225                 230                 235                 240

Lys Thr Lys Pro Arg Glu Glu Gln Tyr Asn Ser Thr Tyr Arg Val Val
                245                 250                 255

Ser Val Leu Thr Val Leu His Gln Asp Trp Leu Asn Gly Lys Glu Tyr
            260                 265                 270

Lys Cys Lys Val Ser Asn Lys Ala Leu Pro Ala Pro Ile Glu Lys Thr
        275                 280                 285

Ile Ser Lys Ala Lys Gly Gln Pro Arg Glu Pro Gln Val Tyr Thr Leu
    290                 295                 300

Pro Pro Ser Arg Glu Glu Met Thr Lys Asn Gln Val Ser Leu Thr Cys
305                 310                 315                 320

Leu Val Lys Gly Phe Tyr Pro Ser Asp Ile Ala Val Glu Trp Glu Ser
                325                 330                 335

Asn Gly Gln Pro Glu Asn Asn Tyr Lys Thr Thr Pro Pro Val Leu Asp
            340                 345                 350

Ser Asp Gly Ser Phe Phe Leu Tyr Ser Lys Leu Thr Val Asp Lys Ser
        355                 360                 365

Arg Trp Gln Gln Gly Asn Val Phe Ser Cys Ser Val Met His Glu Ala
    370                 375                 380

Leu His Asn His Tyr Thr Gln Lys Ser Leu Ser Leu Ser Pro Gly Lys
385                 390                 395                 400

<210> SEQ ID NO 2
<211> LENGTH: 20
<212> TYPE: PRT
<213> ORGANISM: Artificial Sequence
<220> FEATURE:
<223> OTHER INFORMATION: Synthetic signal peptide

<400> SEQUENCE: 2

Met Glu Thr Asp Thr Leu Leu Val Phe Val Leu Leu Val Trp Val Pro
1               5                   10                  15

Ala Gly Asn Gly
            20

<210> SEQ ID NO 3
<211> LENGTH: 382
<212> TYPE: PRT
<213> ORGANISM: Artificial Sequence
<220> FEATURE:
<223> OTHER INFORMATION: Fusion protein consisting of a synthetic
      signal peptide and a functional fragment of the human CD95
      extracellular domain with human IgG1-FC domain fused to its C-
      Terminus.
<220> FEATURE:
<221> NAME/KEY: SIGNAL
<222> LOCATION: (1)..(20)
<220> FEATURE:
<221> NAME/KEY: DOMAIN
<222> LOCATION: (21)..(154)
<223> OTHER INFORMATION: Functional fragment of human CD95 extracellular
      domain
<220> FEATURE:
<221> NAME/KEY: DISULFID
<222> LOCATION: (41)..(55)
<220> FEATURE:
<221> NAME/KEY: DISULFID
<222> LOCATION: (45)..(64)
```

```
<220> FEATURE:
<221> NAME/KEY: DISULFID
<222> LOCATION: (67)..(83)
<220> FEATURE:
<221> NAME/KEY: DISULFID
<222> LOCATION: (86)..(101)
<220> FEATURE:
<221> NAME/KEY: DISULFID
<222> LOCATION: (89)..(109)
<220> FEATURE:
<221> NAME/KEY: CARBOHYD
<222> LOCATION: (100)..(100)
<223> OTHER INFORMATION: N-linked Glycosylation at Position N100
<220> FEATURE:
<221> NAME/KEY: DISULFID
<222> LOCATION: (111)..(125)
<220> FEATURE:
<221> NAME/KEY: DISULFID
<222> LOCATION: (117)..(122)
<220> FEATURE:
<221> NAME/KEY: CARBOHYD
<222> LOCATION: (118)..(118)
<223> OTHER INFORMATION: N-linked Glycosylation at Position N118
<220> FEATURE:
<221> NAME/KEY: DISULFID
<222> LOCATION: (128)..(139)
<220> FEATURE:
<221> NAME/KEY: DISULFID
<222> LOCATION: (131)..(147)
<220> FEATURE:
<221> NAME/KEY: DOMAIN
<222> LOCATION: (154)..(382)
<223> OTHER INFORMATION: Human IgG1-FC domain (one amino acid overlap
      with functional fragment of human CD95 extracellular domain)
<220> FEATURE:
<221> NAME/KEY: DISULFID
<222> LOCATION: (155)..(155)
<223> OTHER INFORMATION: Interchain cystine forming residue
<220> FEATURE:
<221> NAME/KEY: DISULFID
<222> LOCATION: (161)..(161)
<223> OTHER INFORMATION: Interchain cystine forming residue
<220> FEATURE:
<221> NAME/KEY: DISULFID
<222> LOCATION: (164)..(164)
<223> OTHER INFORMATION: Interchain cystine forming residue
<220> FEATURE:
<221> NAME/KEY: DISULFID
<222> LOCATION: (196)..(256)
<220> FEATURE:
<221> NAME/KEY: CARBOHYD
<222> LOCATION: (232)..(232)
<223> OTHER INFORMATION: N-linked Glycosylation at Position N232
<220> FEATURE:
<221> NAME/KEY: DISULFID
<222> LOCATION: (302)..(360)

<400> SEQUENCE: 3

Met Glu Thr Asp Thr Leu Leu Val Phe Val Leu Leu Val Trp Val Pro
1               5                   10                  15

Ala Gly Asn Gly Lys Thr Val Thr Thr Val Glu Thr Gln Asn Leu Glu
            20                  25                  30

Gly Leu His His Asp Gly Gln Phe Cys His Lys Pro Cys Pro Pro Gly
        35                  40                  45

Glu Arg Lys Ala Arg Asp Cys Thr Val Asn Gly Asp Glu Pro Asp Cys
    50                  55                  60

Val Pro Cys Gln Glu Gly Lys Glu Tyr Thr Asp Lys Ala His Phe Ser
65                  70                  75                  80

Ser Lys Cys Arg Arg Cys Arg Leu Cys Asp Glu Gly His Gly Leu Glu
                85                  90                  95

Val Glu Ile Asn Cys Thr Arg Thr Gln Asn Thr Lys Cys Arg Cys Lys
            100                 105                 110
```

Pro Asn Phe Phe Cys Asn Ser Thr Val Cys Glu His Cys Asp Pro Cys
                115                 120                 125

Thr Lys Cys Glu His Gly Ile Ile Lys Glu Cys Thr Leu Thr Ser Asn
        130                 135                 140

Thr Lys Cys Lys Glu Glu Gly Ser Arg Ser Cys Asp Lys Thr His Thr
145                 150                 155                 160

Cys Pro Pro Cys Pro Ala Pro Glu Leu Leu Gly Gly Pro Ser Val Phe
                165                 170                 175

Leu Phe Pro Pro Lys Pro Lys Asp Thr Leu Met Ile Ser Arg Thr Pro
            180                 185                 190

Glu Val Thr Cys Val Val Val Asp Val Ser His Glu Asp Pro Glu Val
                195                 200                 205

Lys Phe Asn Trp Tyr Val Asp Gly Val Glu Val His Asn Ala Lys Thr
        210                 215                 220

Lys Pro Arg Glu Glu Gln Tyr Asn Ser Thr Tyr Arg Val Val Ser Val
225                 230                 235                 240

Leu Thr Val Leu His Gln Asp Trp Leu Asn Gly Lys Glu Tyr Lys Cys
                245                 250                 255

Lys Val Ser Asn Lys Ala Leu Pro Ala Pro Ile Glu Lys Thr Ile Ser
            260                 265                 270

Lys Ala Lys Gly Gln Pro Arg Glu Pro Gln Val Tyr Thr Leu Pro Pro
        275                 280                 285

Ser Arg Glu Glu Met Thr Lys Asn Gln Val Ser Leu Thr Cys Leu Val
            290                 295                 300

Lys Gly Phe Tyr Pro Ser Asp Ile Ala Val Glu Trp Glu Ser Asn Gly
305                 310                 315                 320

Gln Pro Glu Asn Asn Tyr Lys Thr Thr Pro Pro Val Leu Asp Ser Asp
                325                 330                 335

Gly Ser Phe Phe Leu Tyr Ser Lys Leu Thr Val Asp Lys Ser Arg Trp
            340                 345                 350

Gln Gln Gly Asn Val Phe Ser Cys Ser Val Met His Glu Ala Leu His
        355                 360                 365

Asn His Tyr Thr Gln Lys Ser Leu Ser Leu Ser Pro Gly Lys
        370                 375                 380

<210> SEQ ID NO 4
<211> LENGTH: 381
<212> TYPE: PRT
<213> ORGANISM: Artificial Sequence
<220> FEATURE:
<223> OTHER INFORMATION: Fusion protein consisting of a synthetic signal
      peptide and a functional fragment of the human CD95 extracellular
      domain with human IgG1-FC domain fused to its C-Terminus.
<220> FEATURE:
<221> NAME/KEY: SIGNAL
<222> LOCATION: (1)..(20)
<223> OTHER INFORMATION: Synthetic signal peptide
<220> FEATURE:
<221> NAME/KEY: DOMAIN
<222> LOCATION: (21)..(153)
<223> OTHER INFORMATION: Functional fragment of human CD95 extracellular
      domain
<220> FEATURE:
<221> NAME/KEY: DISULFID
<222> LOCATION: (40)..(54)
<220> FEATURE:
<221> NAME/KEY: DISULFID
<222> LOCATION: (44)..(63)
<220> FEATURE:
<221> NAME/KEY: DISULFID
<222> LOCATION: (66)..(82)

```
<220> FEATURE:
<221> NAME/KEY: DISULFID
<222> LOCATION: (85)..(100)
<220> FEATURE:
<221> NAME/KEY: DISULFID
<222> LOCATION: (88)..(108)
<220> FEATURE:
<221> NAME/KEY: CARBOHYD
<222> LOCATION: (99)..(99)
<223> OTHER INFORMATION: N-linked Glycosylation at Position N99
<220> FEATURE:
<221> NAME/KEY: DISULFID
<222> LOCATION: (110)..(124)
<220> FEATURE:
<221> NAME/KEY: DISULFID
<222> LOCATION: (116)..(121)
<220> FEATURE:
<221> NAME/KEY: CARBOHYD
<222> LOCATION: (117)..(117)
<223> OTHER INFORMATION: N-linked Glycosylation at Position N117
<220> FEATURE:
<221> NAME/KEY: DISULFID
<222> LOCATION: (127)..(138)
<220> FEATURE:
<221> NAME/KEY: DISULFID
<222> LOCATION: (130)..(146)
<220> FEATURE:
<221> NAME/KEY: DOMAIN
<222> LOCATION: (153)..(381)
<223> OTHER INFORMATION: Human IgG1-FC domain (one amino acid overlap
     with functional fragment of human CD95 extracellular domain)
<220> FEATURE:
<221> NAME/KEY: DISULFID
<222> LOCATION: (154)..(154)
<223> OTHER INFORMATION: Interchain cystine forming residue
<220> FEATURE:
<221> NAME/KEY: DISULFID
<222> LOCATION: (160)..(160)
<223> OTHER INFORMATION: Interchain cystine forming residue
<220> FEATURE:
<221> NAME/KEY: DISULFID
<222> LOCATION: (163)..(163)
<223> OTHER INFORMATION: Interchain cystine forming residue
<220> FEATURE:
<221> NAME/KEY: DISULFID
<222> LOCATION: (195)..(255)
<220> FEATURE:
<221> NAME/KEY: CARBOHYD
<222> LOCATION: (231)..(231)
<223> OTHER INFORMATION: N-linked Glycosylation at Position N231
<220> FEATURE:
<221> NAME/KEY: DISULFID
<222> LOCATION: (301)..(359)

<400> SEQUENCE: 4

Met Glu Thr Asp Thr Leu Leu Val Phe Val Leu Leu Val Trp Val Pro
1               5                   10                  15

Ala Gly Asn Gly Thr Val Thr Val Glu Thr Gln Asn Leu Glu Gly
            20                  25                  30

Leu His His Asp Gly Gln Phe Cys His Lys Pro Cys Pro Pro Gly Glu
        35                  40                  45

Arg Lys Ala Arg Asp Cys Thr Val Asn Gly Asp Glu Pro Asp Cys Val
    50                  55                  60

Pro Cys Gln Glu Gly Lys Glu Tyr Thr Asp Lys Ala His Phe Ser Ser
65                  70                  75                  80

Lys Cys Arg Arg Cys Arg Leu Cys Asp Glu Gly His Gly Leu Glu Val
                85                  90                  95

Glu Ile Asn Cys Thr Arg Thr Gln Asn Thr Lys Cys Arg Cys Lys Pro
            100                 105                 110

Asn Phe Phe Cys Asn Ser Thr Val Cys Glu His Cys Asp Pro Cys Thr
        115                 120                 125
```

```
Lys Cys Glu His Gly Ile Ile Lys Glu Cys Thr Leu Thr Ser Asn Thr
130                 135                 140
Lys Cys Lys Glu Glu Gly Ser Arg Ser Cys Asp Lys Thr His Thr Cys
145                 150                 155                 160
Pro Pro Cys Pro Ala Pro Glu Leu Leu Gly Gly Pro Ser Val Phe Leu
                165                 170                 175
Phe Pro Pro Lys Pro Lys Asp Thr Leu Met Ile Ser Arg Thr Pro Glu
                180                 185                 190
Val Thr Cys Val Val Val Asp Val Ser His Glu Asp Pro Glu Val Lys
                195                 200                 205
Phe Asn Trp Tyr Val Asp Gly Val Glu Val His Asn Ala Lys Thr Lys
                210                 215                 220
Pro Arg Glu Glu Gln Tyr Asn Ser Thr Tyr Arg Val Val Ser Val Leu
225                 230                 235                 240
Thr Val Leu His Gln Asp Trp Leu Asn Gly Lys Glu Tyr Lys Cys Lys
                245                 250                 255
Val Ser Asn Lys Ala Leu Pro Ala Pro Ile Glu Lys Thr Ile Ser Lys
                260                 265                 270
Ala Lys Gly Gln Pro Arg Glu Pro Gln Val Tyr Thr Leu Pro Pro Ser
                275                 280                 285
Arg Glu Glu Met Thr Lys Asn Gln Val Ser Leu Thr Cys Leu Val Lys
290                 295                 300
Gly Phe Tyr Pro Ser Asp Ile Ala Val Glu Trp Glu Ser Asn Gly Gln
305                 310                 315                 320
Pro Glu Asn Asn Tyr Lys Thr Thr Pro Pro Val Leu Asp Ser Asp Gly
                325                 330                 335
Ser Phe Phe Leu Tyr Ser Lys Leu Thr Val Asp Lys Ser Arg Trp Gln
                340                 345                 350
Gln Gly Asn Val Phe Ser Cys Ser Val Met His Glu Ala Leu His Asn
                355                 360                 365
His Tyr Thr Gln Lys Ser Leu Ser Leu Ser Pro Gly Lys
                370                 375                 380

<210> SEQ ID NO 5
<211> LENGTH: 366
<212> TYPE: PRT
<213> ORGANISM: Artificial Sequence
<220> FEATURE:
<223> OTHER INFORMATION: Fusion protein consisting of a synthetic signal
      peptide and a functional fragment of the human CD95 extracellular
      domain with human IgG1-FC domain fused to its C-Terminus.
<220> FEATURE:
<221> NAME/KEY: SIGNAL
<222> LOCATION: (1)..(20)
<223> OTHER INFORMATION: Synthetic signal peptide
<220> FEATURE:
<221> NAME/KEY: DISULFID
<222> LOCATION: (25)..(39)
<220> FEATURE:
<221> NAME/KEY: DISULFID
<222> LOCATION: (29)..(48)
<220> FEATURE:
<221> NAME/KEY: DISULFID
<222> LOCATION: (51)..(67)
<220> FEATURE:
<221> NAME/KEY: DISULFID
<222> LOCATION: (70)..(85)
<220> FEATURE:
<221> NAME/KEY: DISULFID
<222> LOCATION: (73)..(93)
```

-continued

```
<220> FEATURE:
<221> NAME/KEY: CARBOHYD
<222> LOCATION: (84)..(84)
<223> OTHER INFORMATION: N-linked Glycosylation at Position N84
<220> FEATURE:
<221> NAME/KEY: DISULFID
<222> LOCATION: (95)..(109)
<220> FEATURE:
<221> NAME/KEY: DISULFID
<222> LOCATION: (101)..(106)
<220> FEATURE:
<221> NAME/KEY: CARBOHYD
<222> LOCATION: (102)..(102)
<223> OTHER INFORMATION: N-linked Glycosylation at Position N102
<220> FEATURE:
<221> NAME/KEY: DISULFID
<222> LOCATION: (112)..(123)
<220> FEATURE:
<221> NAME/KEY: DISULFID
<222> LOCATION: (115)..(131)
<220> FEATURE:
<221> NAME/KEY: DOMAIN
<222> LOCATION: (138)..(366)
<223> OTHER INFORMATION: Human IgG1-FC domain (one amino acid overlap
      with functional fragment of human CD95 extracellular domain)
<220> FEATURE:
<221> NAME/KEY: DISULFID
<222> LOCATION: (139)..(139)
<223> OTHER INFORMATION: Interchain cystine forming residue
<220> FEATURE:
<221> NAME/KEY: DISULFID
<222> LOCATION: (145)..(145)
<223> OTHER INFORMATION: Interchain cystine forming residue
<220> FEATURE:
<221> NAME/KEY: DISULFID
<222> LOCATION: (148)..(148)
<223> OTHER INFORMATION: Interchain cystine forming residue
<220> FEATURE:
<221> NAME/KEY: DISULFID
<222> LOCATION: (180)..(240)
<220> FEATURE:
<221> NAME/KEY: CARBOHYD
<222> LOCATION: (216)..(216)
<223> OTHER INFORMATION: N-linked Glycosylation at Position N216
<220> FEATURE:
<221> NAME/KEY: DISULFID
<222> LOCATION: (286)..(344)

<400> SEQUENCE: 5

Met Glu Thr Asp Thr Leu Leu Val Phe Val Leu Leu Val Trp Val Pro
1               5                   10                  15

Ala Gly Asn Gly Asp Gly Gln Phe Cys His Lys Pro Cys Pro Pro Gly
            20                  25                  30

Glu Arg Lys Ala Arg Asp Cys Thr Val Asn Gly Asp Glu Pro Asp Cys
        35                  40                  45

Val Pro Cys Gln Glu Gly Lys Glu Tyr Thr Asp Lys Ala His Phe Ser
    50                  55                  60

Ser Lys Cys Arg Arg Cys Arg Leu Cys Asp Glu Gly His Gly Leu Glu
65                  70                  75                  80

Val Glu Ile Asn Cys Thr Arg Thr Gln Asn Thr Lys Cys Arg Cys Lys
                85                  90                  95

Pro Asn Phe Phe Cys Asn Ser Thr Val Cys Glu His Cys Asp Pro Cys
            100                 105                 110

Thr Lys Cys Glu His Gly Ile Ile Lys Glu Cys Thr Leu Thr Ser Asn
        115                 120                 125

Thr Lys Cys Lys Glu Glu Gly Ser Arg Ser Cys Asp Lys Thr His Thr
    130                 135                 140

Cys Pro Pro Cys Pro Ala Pro Glu Leu Leu Gly Gly Pro Ser Val Phe
145                 150                 155                 160
```

```
Leu Phe Pro Pro Lys Pro Lys Asp Thr Leu Met Ile Ser Arg Thr Pro
            165                 170                 175

Glu Val Thr Cys Val Val Val Asp Val Ser His Glu Asp Pro Glu Val
        180                 185                 190

Lys Phe Asn Trp Tyr Val Asp Gly Val Glu Val His Asn Ala Lys Thr
            195                 200                 205

Lys Pro Arg Glu Glu Gln Tyr Asn Ser Thr Tyr Arg Val Val Ser Val
        210                 215                 220

Leu Thr Val Leu His Gln Asp Trp Leu Asn Gly Lys Glu Tyr Lys Cys
225                 230                 235                 240

Lys Val Ser Asn Lys Ala Leu Pro Ala Pro Ile Glu Lys Thr Ile Ser
                245                 250                 255

Lys Ala Lys Gly Gln Pro Arg Glu Pro Gln Val Tyr Thr Leu Pro Pro
            260                 265                 270

Ser Arg Glu Glu Met Thr Lys Asn Gln Val Ser Leu Thr Cys Leu Val
        275                 280                 285

Lys Gly Phe Tyr Pro Ser Asp Ile Ala Val Glu Trp Glu Ser Asn Gly
            290                 295                 300

Gln Pro Glu Asn Asn Tyr Lys Thr Thr Pro Pro Val Leu Asp Ser Asp
305                 310                 315                 320

Gly Ser Phe Phe Leu Tyr Ser Lys Leu Thr Val Asp Lys Ser Arg Trp
                325                 330                 335

Gln Gln Gly Asn Val Phe Ser Cys Ser Val Met His Glu Ala Leu His
            340                 345                 350

Asn His Tyr Thr Gln Lys Ser Leu Ser Leu Ser Pro Gly Lys
            355                 360                 365

<210> SEQ ID NO 6
<211> LENGTH: 364
<212> TYPE: PRT
<213> ORGANISM: Artificial Sequence
<220> FEATURE:
<223> OTHER INFORMATION: Fusion protein consisting of a synthetic signal
      peptide and a functional fragment of the human CD95 extracellular
      domain with human IgG1-FC domain fused to its C-Terminus.
<220> FEATURE:
<221> NAME/KEY: SIGNAL
<222> LOCATION: (1)..(20)
<223> OTHER INFORMATION: Synthetic signal peptide
<220> FEATURE:
<221> NAME/KEY: DOMAIN
<222> LOCATION: (21)..(136)
<223> OTHER INFORMATION: Functional fragment of human CD95 extracellular
      domain
<220> FEATURE:
<221> NAME/KEY: MOD_RES
<222> LOCATION: (21)..(21)
<223> OTHER INFORMATION: PYRROLIDONE CARBOXYLIC ACID
<220> FEATURE:
<221> NAME/KEY: DISULFID
<222> LOCATION: (23)..(37)
<220> FEATURE:
<221> NAME/KEY: DISULFID
<222> LOCATION: (27)..(46)
<220> FEATURE:
<221> NAME/KEY: DISULFID
<222> LOCATION: (49)..(65)
<220> FEATURE:
<221> NAME/KEY: DISULFID
<222> LOCATION: (68)..(83)
<220> FEATURE:
<221> NAME/KEY: DISULFID
<222> LOCATION: (71)..(91)
```

```
<220> FEATURE:
<221> NAME/KEY: CARBOHYD
<222> LOCATION: (82)..(82)
<223> OTHER INFORMATION: N-linked Glycosylation at Position N98
<220> FEATURE:
<221> NAME/KEY: DISULFID
<222> LOCATION: (93)..(107)
<220> FEATURE:
<221> NAME/KEY: DISULFID
<222> LOCATION: (99)..(104)
<220> FEATURE:
<221> NAME/KEY: CARBOHYD
<222> LOCATION: (100)..(100)
<223> OTHER INFORMATION: N-linked Glycosylation at Position N116
<220> FEATURE:
<221> NAME/KEY: DISULFID
<222> LOCATION: (110)..(121)
<220> FEATURE:
<221> NAME/KEY: DISULFID
<222> LOCATION: (113)..(129)
<220> FEATURE:
<221> NAME/KEY: DOMAIN
<222> LOCATION: (136)..(364)
<223> OTHER INFORMATION: Human IgG1-FC domain (one amino acid overlap
      with functional fragment of human CD95 extracellular domain)
<220> FEATURE:
<221> NAME/KEY: DISULFID
<222> LOCATION: (137)..(137)
<223> OTHER INFORMATION: Interchain cystine forming residue
<220> FEATURE:
<221> NAME/KEY: DISULFID
<222> LOCATION: (143)..(143)
<223> OTHER INFORMATION: Interchain cystine forming residue
<220> FEATURE:
<221> NAME/KEY: DISULFID
<222> LOCATION: (146)..(146)
<223> OTHER INFORMATION: Interchain cystine forming residue
<220> FEATURE:
<221> NAME/KEY: DISULFID
<222> LOCATION: (178)..(238)
<220> FEATURE:
<221> NAME/KEY: CARBOHYD
<222> LOCATION: (214)..(214)
<223> OTHER INFORMATION: N-linked Glycosylation at Position N
<220> FEATURE:
<221> NAME/KEY: DISULFID
<222> LOCATION: (284)..(342)

<400> SEQUENCE: 6

Met Glu Thr Asp Thr Leu Leu Val Phe Val Leu Leu Val Trp Val Pro
 1               5                  10                  15

Ala Gly Asn Gly Gln Phe Cys His Lys Pro Cys Pro Pro Gly Glu Arg
            20                  25                  30

Lys Ala Arg Asp Cys Thr Val Asn Gly Asp Glu Pro Asp Cys Val Pro
        35                  40                  45

Cys Gln Glu Gly Lys Glu Tyr Thr Asp Lys Ala His Phe Ser Ser Lys
    50                  55                  60

Cys Arg Arg Cys Arg Leu Cys Asp Glu Gly His Gly Leu Glu Val Glu
65                  70                  75                  80

Ile Asn Cys Thr Arg Thr Gln Asn Thr Lys Cys Arg Cys Lys Pro Asn
                85                  90                  95

Phe Phe Cys Asn Ser Thr Val Cys Glu His Cys Asp Pro Cys Thr Lys
            100                 105                 110

Cys Glu His Gly Ile Ile Lys Glu Cys Thr Leu Thr Ser Asn Thr Lys
        115                 120                 125

Cys Lys Glu Glu Gly Ser Arg Ser Cys Asp Lys Thr His Thr Cys Pro
    130                 135                 140

Pro Cys Pro Ala Pro Glu Leu Leu Gly Gly Pro Ser Val Phe Leu Phe
145                 150                 155                 160
```

```
Pro Pro Lys Pro Lys Asp Thr Leu Met Ile Ser Arg Thr Pro Glu Val
                165                 170                 175

Thr Cys Val Val Val Asp Val Ser His Glu Asp Pro Glu Val Lys Phe
            180                 185                 190

Asn Trp Tyr Val Asp Gly Val Glu Val His Asn Ala Lys Thr Lys Pro
        195                 200                 205

Arg Glu Glu Gln Tyr Asn Ser Thr Tyr Arg Val Val Ser Val Leu Thr
    210                 215                 220

Val Leu His Gln Asp Trp Leu Asn Gly Lys Glu Tyr Lys Cys Lys Val
225                 230                 235                 240

Ser Asn Lys Ala Leu Pro Ala Pro Ile Glu Lys Thr Ile Ser Lys Ala
                245                 250                 255

Lys Gly Gln Pro Arg Glu Pro Gln Val Tyr Thr Leu Pro Pro Ser Arg
            260                 265                 270

Glu Glu Met Thr Lys Asn Gln Val Ser Leu Thr Cys Leu Val Lys Gly
        275                 280                 285

Phe Tyr Pro Ser Asp Ile Ala Val Glu Trp Glu Ser Asn Gly Gln Pro
    290                 295                 300

Glu Asn Asn Tyr Lys Thr Thr Pro Pro Val Leu Asp Ser Asp Gly Ser
305                 310                 315                 320

Phe Phe Leu Tyr Ser Lys Leu Thr Val Asp Lys Ser Arg Trp Gln Gln
                325                 330                 335

Gly Asn Val Phe Ser Cys Ser Val Met His Glu Ala Leu His Asn His
            340                 345                 350

Tyr Thr Gln Lys Ser Leu Ser Leu Ser Pro Gly Lys
        355                 360

<210> SEQ ID NO 7
<211> LENGTH: 147
<212> TYPE: PRT
<213> ORGANISM: human

<400> SEQUENCE: 7

Gln Val Thr Asp Ile Asn Ser Lys Gly Leu Glu Leu Arg Lys Thr Val
1               5                   10                  15

Thr Thr Val Glu Thr Gln Asn Leu Glu Gly Leu His His Asp Gly Gln
            20                  25                  30

Phe Cys His Lys Pro Cys Pro Pro Gly Glu Arg Lys Ala Arg Asp Cys
        35                  40                  45

Thr Val Asn Gly Asp Glu Pro Asp Cys Val Pro Cys Gln Glu Gly Lys
    50                  55                  60

Glu Tyr Thr Asp Lys Ala His Phe Ser Ser Lys Cys Arg Arg Cys Arg
65                  70                  75                  80

Leu Cys Asp Glu Gly His Gly Leu Glu Val Glu Ile Asn Cys Thr Arg
                85                  90                  95

Thr Gln Asn Thr Lys Cys Arg Cys Lys Pro Asn Phe Phe Cys Asn Ser
            100                 105                 110

Thr Val Cys Glu His Cys Asp Pro Cys Thr Lys Cys Glu His Gly Ile
        115                 120                 125

Ile Lys Glu Cys Thr Leu Thr Ser Asn Thr Lys Cys Lys Glu Glu Gly
    130                 135                 140

Ser Arg Ser
145
```

```
<210> SEQ ID NO 8
<211> LENGTH: 229
<212> TYPE: PRT
<213> ORGANISM: human

<400> SEQUENCE: 8

Ser Cys Asp Lys Thr His Thr Cys Pro Pro Cys Pro Ala Pro Glu Leu
1               5                   10                  15

Leu Gly Gly Pro Ser Val Phe Leu Phe Pro Pro Lys Pro Lys Asp Thr
            20                  25                  30

Leu Met Ile Ser Arg Thr Pro Glu Val Thr Cys Val Val Val Asp Val
        35                  40                  45

Ser His Glu Asp Pro Glu Val Lys Phe Asn Trp Tyr Val Asp Gly Val
    50                  55                  60

Glu Val His Asn Ala Lys Thr Lys Pro Arg Glu Glu Gln Tyr Asn Ser
65                  70                  75                  80

Thr Tyr Arg Val Val Ser Val Leu Thr Val Leu His Gln Asp Trp Leu
                85                  90                  95

Asn Gly Lys Glu Tyr Lys Cys Lys Val Ser Asn Lys Ala Leu Pro Ala
            100                 105                 110

Pro Ile Glu Lys Thr Ile Ser Lys Ala Lys Gly Gln Pro Arg Glu Pro
        115                 120                 125

Gln Val Tyr Thr Leu Pro Pro Ser Arg Glu Glu Met Thr Lys Asn Gln
    130                 135                 140

Val Ser Leu Thr Cys Leu Val Lys Gly Phe Tyr Pro Ser Asp Ile Ala
145                 150                 155                 160

Val Glu Trp Glu Ser Asn Gly Gln Pro Glu Asn Asn Tyr Lys Thr Thr
                165                 170                 175

Pro Pro Val Leu Asp Ser Asp Gly Ser Phe Phe Leu Tyr Ser Lys Leu
            180                 185                 190

Thr Val Asp Lys Ser Arg Trp Gln Gln Gly Asn Val Phe Ser Cys Ser
        195                 200                 205

Val Met His Glu Ala Leu His Asn His Tyr Thr Gln Lys Ser Leu Ser
    210                 215                 220

Leu Ser Pro Gly Lys
225

<210> SEQ ID NO 9
<211> LENGTH: 134
<212> TYPE: PRT
<213> ORGANISM: artificial
<220> FEATURE:
<223> OTHER INFORMATION: truncated human CD95 (position 21 to 154 of SEQ
      ID NO:3)

<400> SEQUENCE: 9

Lys Thr Val Thr Thr Val Glu Thr Gln Asn Leu Glu Gly Leu His His
1               5                   10                  15

Asp Gly Gln Phe Cys His Lys Pro Cys Pro Pro Gly Glu Arg Lys Ala
            20                  25                  30

Arg Asp Cys Thr Val Asn Gly Asp Glu Pro Asp Cys Val Pro Cys Gln
        35                  40                  45

Glu Gly Lys Glu Tyr Thr Asp Lys Ala His Phe Ser Ser Lys Cys Arg
    50                  55                  60

Arg Cys Arg Leu Cys Asp Glu Gly His Gly Leu Glu Val Glu Ile Asn
65                  70                  75                  80
```

```
Cys Thr Arg Thr Gln Asn Thr Lys Cys Arg Cys Lys Pro Asn Phe Phe
                85                  90                  95

Cys Asn Ser Thr Val Cys Glu His Cys Asp Pro Cys Thr Lys Cys Glu
            100                 105                 110

His Gly Ile Ile Lys Glu Cys Thr Leu Thr Ser Asn Thr Lys Cys Lys
        115                 120                 125

Glu Glu Gly Ser Arg Ser
        130

<210> SEQ ID NO 10
<211> LENGTH: 133
<212> TYPE: PRT
<213> ORGANISM: artificial
<220> FEATURE:
<223> OTHER INFORMATION: truncated human CD95 (position 21 to 153 of SEQ
      ID NO:4)

<400> SEQUENCE: 10

Thr Val Thr Thr Val Glu Thr Gln Asn Leu Glu Gly Leu His His Asp
1               5                   10                  15

Gly Gln Phe Cys His Lys Pro Cys Pro Pro Gly Glu Arg Lys Ala Arg
            20                  25                  30

Asp Cys Thr Val Asn Gly Asp Glu Pro Asp Cys Val Pro Cys Gln Glu
        35                  40                  45

Gly Lys Glu Tyr Thr Asp Lys Ala His Phe Ser Ser Lys Cys Arg Arg
    50                  55                  60

Cys Arg Leu Cys Asp Glu Gly His Gly Leu Glu Val Glu Ile Asn Cys
65                  70                  75                  80

Thr Arg Thr Gln Asn Thr Lys Cys Arg Cys Lys Pro Asn Phe Phe Cys
                85                  90                  95

Asn Ser Thr Val Cys Glu His Cys Asp Pro Cys Thr Lys Cys Glu His
            100                 105                 110

Gly Ile Ile Lys Glu Cys Thr Leu Thr Ser Asn Thr Lys Cys Lys Glu
        115                 120                 125

Glu Gly Ser Arg Ser
    130

<210> SEQ ID NO 11
<211> LENGTH: 118
<212> TYPE: PRT
<213> ORGANISM: artificial
<220> FEATURE:
<223> OTHER INFORMATION: truncated human CD95 (position 21 to 138 of SEQ
      ID NO:5)

<400> SEQUENCE: 11

Asp Gly Gln Phe Cys His Lys Pro Cys Pro Pro Gly Glu Arg Lys Ala
1               5                   10                  15

Arg Asp Cys Thr Val Asn Gly Asp Glu Pro Asp Cys Val Pro Cys Gln
            20                  25                  30

Glu Gly Lys Glu Tyr Thr Asp Lys Ala His Phe Ser Ser Lys Cys Arg
        35                  40                  45

Arg Cys Arg Leu Cys Asp Glu Gly His Gly Leu Glu Val Glu Ile Asn
    50                  55                  60

Cys Thr Arg Thr Gln Asn Thr Lys Cys Arg Cys Lys Pro Asn Phe Phe
65                  70                  75                  80

Cys Asn Ser Thr Val Cys Glu His Cys Asp Pro Cys Thr Lys Cys Glu
                85                  90                  95
```

-continued

His Gly Ile Ile Lys Glu Cys Thr Leu Thr Ser Asn Thr Lys Cys Lys
                100                 105                 110

Glu Glu Gly Ser Arg Ser
        115

<210> SEQ ID NO 12
<211> LENGTH: 116
<212> TYPE: PRT
<213> ORGANISM: artificial
<220> FEATURE:
<223> OTHER INFORMATION: truncated human CD95 (position 21 to 136 of SEQ
      ID NO.6)

<400> SEQUENCE: 12

Gln Phe Cys His Lys Pro Cys Pro Pro Gly Glu Arg Lys Ala Arg Asp
1               5                   10                  15

Cys Thr Val Asn Gly Asp Glu Pro Asp Cys Val Pro Cys Gln Glu Gly
            20                  25                  30

Lys Glu Tyr Thr Asp Lys Ala His Phe Ser Ser Lys Cys Arg Arg Cys
        35                  40                  45

Arg Leu Cys Asp Glu Gly His Gly Leu Glu Val Glu Ile Asn Cys Thr
    50                  55                  60

Arg Thr Gln Asn Thr Lys Cys Arg Cys Lys Pro Asn Phe Phe Cys Asn
65                  70                  75                  80

Ser Thr Val Cys Glu His Cys Asp Pro Cys Thr Lys Cys Glu His Gly
                85                  90                  95

Ile Ile Lys Glu Cys Thr Leu Thr Ser Asn Thr Lys Cys Lys Glu Glu
            100                 105                 110

Gly Ser Arg Ser
        115

<210> SEQ ID NO 13
<211> LENGTH: 25
<212> TYPE: PRT
<213> ORGANISM: artificial
<220> FEATURE:
<223> OTHER INFORMATION: modified human CD95 signal peptide

<400> SEQUENCE: 13

Met Val Gly Ile Trp Thr Leu Leu Pro Leu Val Leu Thr Ser Val Ala
1               5                   10                  15

Arg Leu Ser Ser Lys Ser Val Asn Ala
            20                  25

<210> SEQ ID NO 14
<211> LENGTH: 25
<212> TYPE: PRT
<213> ORGANISM: human

<400> SEQUENCE: 14

Met Leu Gly Ile Trp Thr Leu Leu Pro Leu Val Leu Thr Ser Val Ala
1               5                   10                  15

Arg Leu Ser Ser Lys Ser Val Asn Ala
            20                  25

<210> SEQ ID NO 15
<211> LENGTH: 375
<212> TYPE: PRT
<213> ORGANISM: artificial
<220> FEATURE:
<223> OTHER INFORMATION: mature APG101 (position 26-400 of SEQ ID NO:1)

<400> SEQUENCE: 15

```
Gln Val Thr Asp Ile Asn Ser Lys Gly Leu Glu Leu Arg Lys Thr Val
1               5                   10                  15

Thr Thr Val Glu Thr Gln Asn Leu Glu Gly Leu His His Asp Gly Gln
            20                  25                  30

Phe Cys His Lys Pro Cys Pro Pro Gly Glu Arg Lys Ala Arg Asp Cys
        35                  40                  45

Thr Val Asn Gly Asp Glu Pro Asp Cys Val Pro Cys Gln Glu Gly Lys
    50                  55                  60

Glu Tyr Thr Asp Lys Ala His Phe Ser Ser Lys Cys Arg Arg Cys Arg
65                  70                  75                  80

Leu Cys Asp Glu Gly His Gly Leu Glu Val Glu Ile Asn Cys Thr Arg
            85                  90                  95

Thr Gln Asn Thr Lys Cys Arg Cys Lys Pro Asn Phe Phe Cys Asn Ser
        100                 105                 110

Thr Val Cys Glu His Cys Asp Pro Cys Thr Lys Cys Glu His Gly Ile
    115                 120                 125

Ile Lys Glu Cys Thr Leu Thr Ser Asn Thr Lys Cys Lys Glu Glu Gly
130                 135                 140

Ser Arg Ser Cys Asp Lys Thr His Thr Cys Pro Pro Cys Pro Ala Pro
145                 150                 155                 160

Glu Leu Leu Gly Gly Pro Ser Val Phe Leu Phe Pro Pro Lys Pro Lys
            165                 170                 175

Asp Thr Leu Met Ile Ser Arg Thr Pro Glu Val Thr Cys Val Val Val
        180                 185                 190

Asp Val Ser His Glu Asp Pro Glu Val Lys Phe Asn Trp Tyr Val Asp
    195                 200                 205

Gly Val Glu Val His Asn Ala Lys Thr Lys Pro Arg Glu Glu Gln Tyr
            210                 215                 220

Asn Ser Thr Tyr Arg Val Val Ser Val Leu Thr Val Leu His Gln Asp
225                 230                 235                 240

Trp Leu Asn Gly Lys Glu Tyr Lys Cys Lys Val Ser Asn Lys Ala Leu
            245                 250                 255

Pro Ala Pro Ile Glu Lys Thr Ile Ser Lys Ala Lys Gly Gln Pro Arg
        260                 265                 270

Glu Pro Gln Val Tyr Thr Leu Pro Pro Ser Arg Glu Glu Met Thr Lys
    275                 280                 285

Asn Gln Val Ser Leu Thr Cys Leu Val Lys Gly Phe Tyr Pro Ser Asp
290                 295                 300

Ile Ala Val Glu Trp Glu Ser Asn Gly Gln Pro Glu Asn Asn Tyr Lys
305                 310                 315                 320

Thr Thr Pro Pro Val Leu Asp Ser Asp Gly Ser Phe Phe Leu Tyr Ser
            325                 330                 335

Lys Leu Thr Val Asp Lys Ser Arg Trp Gln Gln Gly Asn Val Phe Ser
        340                 345                 350

Cys Ser Val Met His Glu Ala Leu His Asn His Tyr Thr Gln Lys Ser
    355                 360                 365

Leu Ser Leu Ser Pro Gly Lys
    370                 375
```

<210> SEQ ID NO 16
<211> LENGTH: 362
<212> TYPE: PRT
<213> ORGANISM: artificial

<220> FEATURE:
<223> OTHER INFORMATION: mature APG130 (position 21 to 382 of SEQ ID NO:3)

<400> SEQUENCE: 16

```
Lys Thr Val Thr Thr Val Glu Thr Gln Asn Leu Glu Gly Leu His His
1               5                   10                  15

Asp Gly Gln Phe Cys His Lys Pro Cys Pro Pro Gly Glu Arg Lys Ala
            20                  25                  30

Arg Asp Cys Thr Val Asn Gly Asp Glu Pro Asp Cys Val Pro Cys Gln
        35                  40                  45

Glu Gly Lys Glu Tyr Thr Asp Lys Ala His Phe Ser Ser Lys Cys Arg
    50                  55                  60

Arg Cys Arg Leu Cys Asp Glu Gly His Gly Leu Glu Val Glu Ile Asn
65                  70                  75                  80

Cys Thr Arg Thr Gln Asn Thr Lys Cys Arg Cys Lys Pro Asn Phe Phe
                85                  90                  95

Cys Asn Ser Thr Val Cys Glu His Cys Asp Pro Cys Thr Lys Cys Glu
            100                 105                 110

His Gly Ile Ile Lys Glu Cys Thr Leu Thr Ser Asn Thr Lys Cys Lys
        115                 120                 125

Glu Glu Gly Ser Arg Ser Cys Asp Lys Thr His Thr Cys Pro Pro Cys
    130                 135                 140

Pro Ala Pro Glu Leu Leu Gly Gly Pro Ser Val Phe Leu Phe Pro Pro
145                 150                 155                 160

Lys Pro Lys Asp Thr Leu Met Ile Ser Arg Thr Pro Glu Val Thr Cys
                165                 170                 175

Val Val Val Asp Val Ser His Glu Asp Pro Glu Val Lys Phe Asn Trp
            180                 185                 190

Tyr Val Asp Gly Val Glu Val His Asn Ala Lys Thr Lys Pro Arg Glu
        195                 200                 205

Glu Gln Tyr Asn Ser Thr Tyr Arg Val Val Ser Val Leu Thr Val Leu
    210                 215                 220

His Gln Asp Trp Leu Asn Gly Lys Glu Tyr Lys Cys Lys Val Ser Asn
225                 230                 235                 240

Lys Ala Leu Pro Ala Pro Ile Glu Lys Thr Ile Ser Lys Ala Lys Gly
                245                 250                 255

Gln Pro Arg Glu Pro Gln Val Tyr Thr Leu Pro Pro Ser Arg Glu Glu
            260                 265                 270

Met Thr Lys Asn Gln Val Ser Leu Thr Cys Leu Val Lys Gly Phe Tyr
        275                 280                 285

Pro Ser Asp Ile Ala Val Glu Trp Glu Ser Asn Gly Gln Pro Glu Asn
    290                 295                 300

Asn Tyr Lys Thr Thr Pro Pro Val Leu Asp Ser Asp Gly Ser Phe Phe
305                 310                 315                 320

Leu Tyr Ser Lys Leu Thr Val Asp Lys Ser Arg Trp Gln Gln Gly Asn
                325                 330                 335

Val Phe Ser Cys Ser Val Met His Glu Ala Leu His Asn His Tyr Thr
            340                 345                 350

Gln Lys Ser Leu Ser Leu Ser Pro Gly Lys
        355                 360
```

```
<210> SEQ ID NO 17
<211> LENGTH: 361
<212> TYPE: PRT
<213> ORGANISM: artificial
<220> FEATURE:
<223> OTHER INFORMATION: mature APG 131 (position 21 to 381 of SEQ ID
      NO:4)

<400> SEQUENCE: 17

Thr Val Thr Thr Val Glu Thr Gln Asn Leu Glu Gly Leu His His Asp
1               5                   10                  15

Gly Gln Phe Cys His Lys Pro Cys Pro Pro Gly Glu Arg Lys Ala Arg
            20                  25                  30

Asp Cys Thr Val Asn Gly Asp Glu Pro Asp Cys Val Pro Cys Gln Glu
        35                  40                  45

Gly Lys Glu Tyr Thr Asp Lys Ala His Phe Ser Ser Lys Cys Arg Arg
    50                  55                  60

Cys Arg Leu Cys Asp Glu Gly His Gly Leu Glu Val Glu Ile Asn Cys
65                  70                  75                  80

Thr Arg Thr Gln Asn Thr Lys Cys Arg Cys Lys Pro Asn Phe Phe Cys
                85                  90                  95

Asn Ser Thr Val Cys Glu His Cys Asp Pro Cys Thr Lys Cys Glu His
            100                 105                 110

Gly Ile Ile Lys Glu Cys Thr Leu Thr Ser Asn Thr Lys Cys Lys Glu
        115                 120                 125

Glu Gly Ser Arg Ser Cys Asp Lys Thr His Thr Cys Pro Pro Cys Pro
    130                 135                 140

Ala Pro Glu Leu Leu Gly Gly Pro Ser Val Phe Leu Phe Pro Pro Lys
145                 150                 155                 160

Pro Lys Asp Thr Leu Met Ile Ser Arg Thr Pro Glu Val Thr Cys Val
                165                 170                 175

Val Val Asp Val Ser His Glu Asp Pro Glu Val Lys Phe Asn Trp Tyr
            180                 185                 190

Val Asp Gly Val Glu Val His Asn Ala Lys Thr Lys Pro Arg Glu Glu
        195                 200                 205

Gln Tyr Asn Ser Thr Tyr Arg Val Val Ser Val Leu Thr Val Leu His
    210                 215                 220

Gln Asp Trp Leu Asn Gly Lys Glu Tyr Lys Cys Lys Val Ser Asn Lys
225                 230                 235                 240

Ala Leu Pro Ala Pro Ile Glu Lys Thr Ile Ser Lys Ala Lys Gly Gln
                245                 250                 255

Pro Arg Glu Pro Gln Val Tyr Thr Leu Pro Pro Ser Arg Glu Glu Met
            260                 265                 270

Thr Lys Asn Gln Val Ser Leu Thr Cys Leu Val Lys Gly Phe Tyr Pro
        275                 280                 285

Ser Asp Ile Ala Val Glu Trp Glu Ser Asn Gly Gln Pro Glu Asn Asn
    290                 295                 300

Tyr Lys Thr Thr Pro Pro Val Leu Asp Ser Asp Gly Ser Phe Phe Leu
305                 310                 315                 320

Tyr Ser Lys Leu Thr Val Asp Lys Ser Arg Trp Gln Gln Gly Asn Val
                325                 330                 335

Phe Ser Cys Ser Val Met His Glu Ala Leu His Asn His Tyr Thr Gln
            340                 345                 350

Lys Ser Leu Ser Leu Ser Pro Gly Lys
        355                 360
```

-continued

```
<210> SEQ ID NO 18
<211> LENGTH: 346
<212> TYPE: PRT
<213> ORGANISM: artificial
<220> FEATURE:
<223> OTHER INFORMATION: mature APG 132 (position 21 to 366 of SEQ ID
      NO:5)

<400> SEQUENCE: 18

Asp Gly Gln Phe Cys His Lys Pro Cys Pro Gly Glu Arg Lys Ala
1               5                   10                  15

Arg Asp Cys Thr Val Asn Gly Asp Glu Pro Asp Cys Val Pro Cys Gln
                20                  25                  30

Glu Gly Lys Glu Tyr Thr Asp Lys Ala His Phe Ser Ser Lys Cys Arg
            35                  40                  45

Arg Cys Arg Leu Cys Asp Glu Gly His Gly Leu Glu Val Glu Ile Asn
        50                  55                  60

Cys Thr Arg Thr Gln Asn Thr Lys Cys Arg Cys Lys Pro Asn Phe Phe
65                  70                  75                  80

Cys Asn Ser Thr Val Cys Glu His Cys Asp Pro Cys Thr Lys Cys Glu
                85                  90                  95

His Gly Ile Ile Lys Glu Cys Thr Leu Thr Ser Asn Thr Lys Cys Lys
            100                 105                 110

Glu Glu Gly Ser Arg Ser Cys Asp Lys Thr His Thr Cys Pro Pro Cys
        115                 120                 125

Pro Ala Pro Glu Leu Leu Gly Gly Pro Ser Val Phe Leu Phe Pro Pro
130                 135                 140

Lys Pro Lys Asp Thr Leu Met Ile Ser Arg Thr Pro Glu Val Thr Cys
145                 150                 155                 160

Val Val Val Asp Val Ser His Glu Asp Pro Glu Val Lys Phe Asn Trp
                165                 170                 175

Tyr Val Asp Gly Val Glu Val His Asn Ala Lys Thr Lys Pro Arg Glu
            180                 185                 190

Glu Gln Tyr Asn Ser Thr Tyr Arg Val Val Ser Val Leu Thr Val Leu
        195                 200                 205

His Gln Asp Trp Leu Asn Gly Lys Glu Tyr Lys Cys Lys Val Ser Asn
210                 215                 220

Lys Ala Leu Pro Ala Pro Ile Glu Lys Thr Ile Ser Lys Ala Lys Gly
225                 230                 235                 240

Gln Pro Arg Glu Pro Gln Val Tyr Thr Leu Pro Pro Ser Arg Glu Glu
                245                 250                 255

Met Thr Lys Asn Gln Val Ser Leu Thr Cys Leu Val Lys Gly Phe Tyr
            260                 265                 270

Pro Ser Asp Ile Ala Val Glu Trp Glu Ser Asn Gly Gln Pro Glu Asn
        275                 280                 285

Asn Tyr Lys Thr Thr Pro Pro Val Leu Asp Ser Asp Gly Ser Phe Phe
290                 295                 300

Leu Tyr Ser Lys Leu Thr Val Asp Lys Ser Arg Trp Gln Gln Gly Asn
305                 310                 315                 320

Val Phe Ser Cys Ser Val Met His Glu Ala Leu His Asn His Tyr Thr
                325                 330                 335

Gln Lys Ser Leu Ser Leu Ser Pro Gly Lys
            340                 345
```

```
<210> SEQ ID NO 19
<211> LENGTH: 344
<212> TYPE: PRT
<213> ORGANISM: artificial
<220> FEATURE:
<223> OTHER INFORMATION: mature APG 133 (position 21 to 364 of SEQ ID
      NO:6)

<400> SEQUENCE: 19

Gln Phe Cys His Lys Pro Cys Pro Pro Gly Glu Arg Lys Ala Arg Asp
1               5                   10                  15

Cys Thr Val Asn Gly Asp Glu Pro Asp Cys Val Pro Cys Gln Glu Gly
                20                  25                  30

Lys Glu Tyr Thr Asp Lys Ala His Phe Ser Ser Lys Cys Arg Arg Cys
            35                  40                  45

Arg Leu Cys Asp Glu Gly His Gly Leu Glu Val Glu Ile Asn Cys Thr
    50                  55                  60

Arg Thr Gln Asn Thr Lys Cys Arg Cys Lys Pro Asn Phe Phe Cys Asn
65                  70                  75                  80

Ser Thr Val Cys Glu His Cys Asp Pro Cys Thr Lys Cys Glu His Gly
                85                  90                  95

Ile Ile Lys Glu Cys Thr Leu Thr Ser Asn Thr Lys Cys Lys Glu Glu
            100                 105                 110

Gly Ser Arg Ser Cys Asp Lys Thr His Thr Cys Pro Pro Cys Pro Ala
        115                 120                 125

Pro Glu Leu Leu Gly Gly Pro Ser Val Phe Leu Phe Pro Pro Lys Pro
    130                 135                 140

Lys Asp Thr Leu Met Ile Ser Arg Thr Pro Glu Val Thr Cys Val Val
145                 150                 155                 160

Val Asp Val Ser His Glu Asp Pro Glu Val Lys Phe Asn Trp Tyr Val
                165                 170                 175

Asp Gly Val Glu Val His Asn Ala Lys Thr Lys Pro Arg Glu Glu Gln
            180                 185                 190

Tyr Asn Ser Thr Tyr Arg Val Val Ser Val Leu Thr Val Leu His Gln
        195                 200                 205

Asp Trp Leu Asn Gly Lys Glu Tyr Lys Cys Lys Val Ser Asn Lys Ala
    210                 215                 220

Leu Pro Ala Pro Ile Glu Lys Thr Ile Ser Lys Ala Lys Gly Gln Pro
225                 230                 235                 240

Arg Glu Pro Gln Val Tyr Thr Leu Pro Pro Ser Arg Glu Glu Met Thr
                245                 250                 255

Lys Asn Gln Val Ser Leu Thr Cys Leu Val Lys Gly Phe Tyr Pro Ser
            260                 265                 270

Asp Ile Ala Val Glu Trp Glu Ser Asn Gly Gln Pro Glu Asn Asn Tyr
        275                 280                 285

Lys Thr Thr Pro Pro Val Leu Asp Ser Asp Gly Ser Phe Phe Leu Tyr
    290                 295                 300

Ser Lys Leu Thr Val Asp Lys Ser Arg Trp Gln Gln Gly Asn Val Phe
305                 310                 315                 320

Ser Cys Ser Val Met His Glu Ala Leu His Asn His Tyr Thr Gln Lys
                325                 330                 335

Ser Leu Ser Leu Ser Pro Gly Lys
            340
```

ARTIFICIAL SIGNAL PEPTIDE

This application is a divisional of U.S. application Ser. No. 14/415,871, filed Jan. 20, 2015, now U.S. Pat. No. 9,434,783; which is a National Stage of PCT/EP2013/065248, filed Jul. 18, 2013, published Jan. 23, 2014, under PCT Article 21(2) in English; which claims the priority of EP 12176980.6 and EP 12176978.0, both filed Jul. 18, 2012. The contents of the above applications are incorporated herein by reference in their entirety.

REFERENCE TO SEQUENCE LISTING, TABLE OR COMPUTER PROGRAM

The Sequence Listing is concurrently submitted herewith with the specification as an ASCII formatted text file via EFS-Web with a file name of Sequence Listing with a creation date of Mar. 10, 2015, and a size of 48.7 kilobytes. The Sequence Listing filed via EFS-Web is part of the specification and is hereby incorporated in its entirety by reference herein.

TECHNICAL FIELD

The present invention relates to an isolated fusion protein comprising an extracellular CD95 domain or a functional fragment thereof and an Fc domain or functional fragment thereof, formulations providing such fusion protein in a stable form as well as a method for producing such a fusion protein.

BRIEF DESCRIPTION OF THE DRAWINGS

FIG. 4b: IEF of AEX fraction of an APG101 mixture obtained by the non-inventive method.

DETAILED DESCRIPTION OF THE INVENTION

Figure 1:
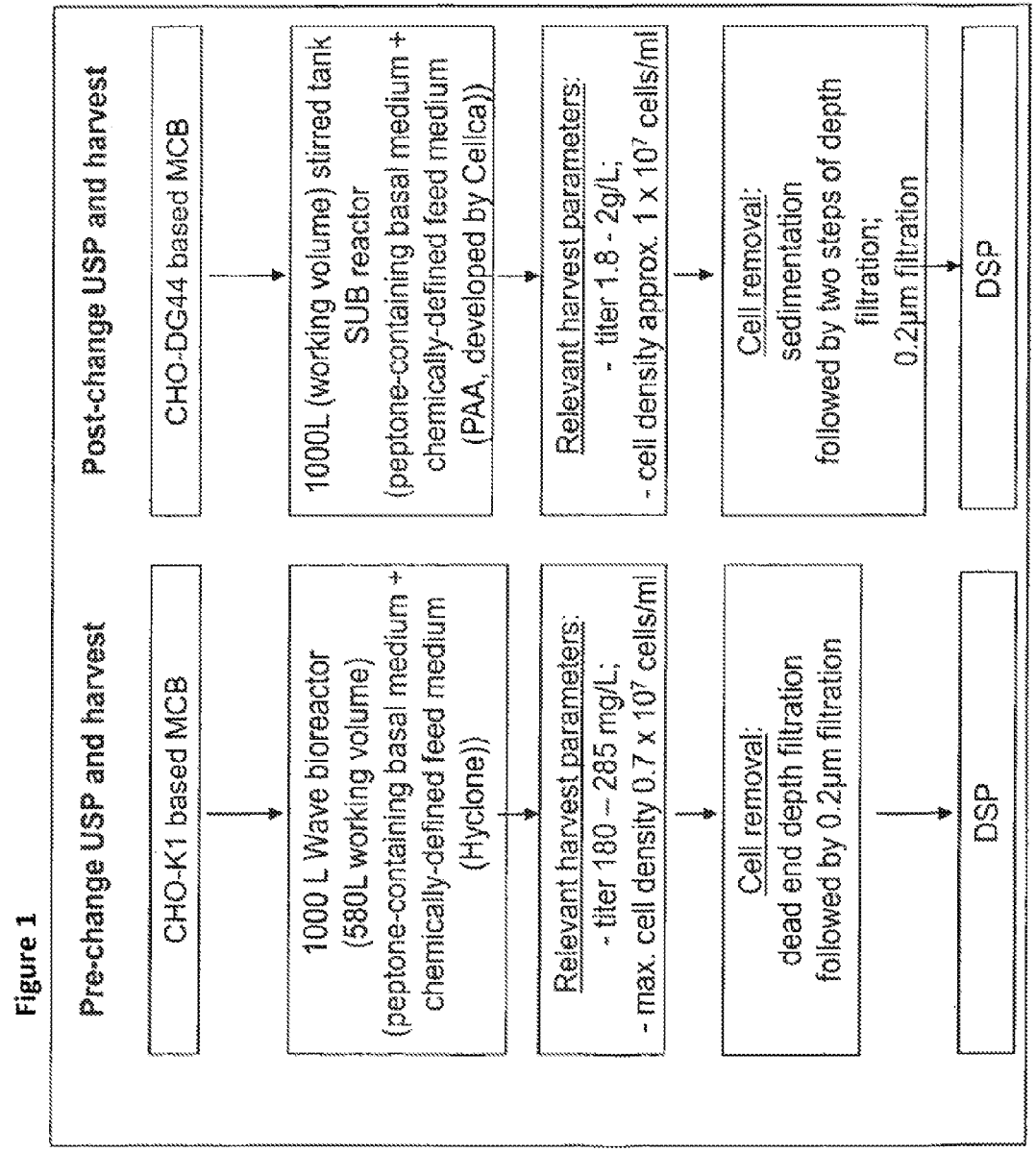
FIG. 1: Comparison of the inventive upstream process with a non-inventive upstream process

Fusion proteins comprising the extracellular domain of the death receptor CD95 (Apo-1; Fas) fused to an immunoglobulin Fc domain are described in PCT/EP04/03239. However, it turned out difficult to provide such fusion proteins in sufficient amounts with a sufficient stability.

With the present invention it is possible for the first time to provide such compositions or methods.

According to a first aspect the present invention relates to a composition comprising a mixture of fusion protein isoforms, each fusion protein comprising at least an extracellular CD95 domain (APO-1; Fas) or a functional fragment thereof and at least a second domain being an Fc domain or a functional fragment thereof distributing within a pI range of about 4.0 to about 8.5. Accordingly, the extracellular CD95 domain as used herein may be also called "first domain", while the Fc domain may be called "second domain".

The first domain protein is an extracellular CD95 domain, preferably a mammalian extracellular domain, in particular a human protein, i.e. a human extracellular CD95 domain. The first domain, i.e. the extracellular CD95 domain, of the fusion protein preferably comprises the amino acid sequence up to amino acid 170, 171, 172 or 173 of human CD95 (SEQ ID NO. 1). A signal peptide (e.g. position 1-25 of SEQ ID NO: 1) may be present or not.

Particularly for therapeutic purposes the use of a human protein is preferred.

The fusion protein can comprise one or more first domains which may be the same or different. However, one first domain, i.e. a fusion protein comprising one extracellular CD95 domain is preferred.

According to a preferred embodiment, the Fc domain or functional fragment thereof, i.e. the second domain of the fusion protein according to the invention, comprises the CH2 and/or CH3 domain, and optionally at least a part of the hinge region. domain or a modified immunoglobulin domain derived therefrom. The immunoglobulin domain may be an IgG, IgM, IgD, or IgE immunoglobulin domain or a modified immunoglobulin domain derived, therefrom. Preferably, the second domain comprises at least a portion of a constant IgG immunoglobulin domain. The IgG immunoglobulin domain may be selected from IgG1, IgG2, IgG3 or IgG4 domains or from modified domains therefrom. Preferably, the second domain is a human Fc domain, such as a IgG Fc domain, e.g. a human IgG1 Fc domain.

The fusion protein can comprise one or more second domains which may be the same or different. However, one second domain, i.e. a fusion protein comprising one Fc domain is preferred.

Further, both the first and second domains are preferably from the same species.

The first domain, i.e. the extracellular CD95 domain or the functional fragment thereof may be located at the N- or C-terminus. The second domain, i.e. the Fc domain or functional fragment may also be located at the C- or N-terminus of the fusion protein. However, the extracellular CD95 domain at the N-terminus of the fusion protein is preferred.

According to a further preferred embodiment, the fusion protein is APG101 (CD95-Fc, position 26-400 in SEQ ID NO: 1). As defined by SEQ ID NO: 1 APG101 can be a fusion protein comprising a human extracellular CD95 domain (amino acids 26-172) and a human IgG1 Fc domain (amino acids 172-400), further optionally comprising an N-terminal signal sequence (e.g. amino acids 1-25 of SEQ ID NO: 1). The presence of the signal peptide indicates the immature form of APG101. During maturation, the signal peptide is cleaved off. According to an especially preferred embodiment the signal sequence is cleaved off. APG101 with the signal sequence is also comprised by the term "unmodified APG101". In a further embodiment the fusion protein is a polypeptide having at least 70% identity, more preferably 75% identity, 80% identity, 85% identity, 90% identity, 95% identity, 96% identity, 97% identity, 98% identity, 99% identity with APG101. According to the present application the term "identity" relates to the extent to which two amino acid sequences being compared are invariant, in other words share the same amino acids in the same position.

The term "APG101" describes a fusion protein of position 26-400 of SEQ ID NO: 1, with and without a signal peptide. The term "APG101" also includes fusion proteins containing N-terminally truncated forms of the CD95 extracellular domain.

In another preferred embodiment the fusion protein according to the invention is a functional fragment of APG101. As used herein, the term "fragment" generally designates a "functional fragment", i.e. a fragment or portion of a wild-type or full-length protein which has essentially the same biological activity and/or properties as the corresponding wild-type or full-length protein has.

A person skilled in the art is aware of methods to design and produce fusion proteins according to the present invention. The mixture of fusion protein isoforms, in particular APG101 isoforms, however, is obtained by the method described herein below. Such methods are described, e.g., in PCT/EP04/03239. According to a preferred embodiment designing a fusion protein of the present invention comprises a selection of the terminal amino acid(s) of the first domain and of the second domain in order to create at least one amino acid overlap between both domains. The overlap between the first and the second domain or between the two first domains has a length of preferably 1, 2 or 3 amino acids. More preferably, the overlap has a length of one amino acid. Examples for overlapping amino acids are S, E, K, H, T, P, and D.

The composition according to the invention comprises a mixture of protein isoforms. The term "isoform" as used herein designates different forms of the same protein, such as different forms of APG101, in particular APG101 without signal sequence. Such isoforms can differ, for example, by protein length, by amino acid, i.e. Substitution and/or deletion, and/or post-translational modification when compared to the corresponding unmodified protein, i.e. The protein which is translated and expressed from a given coding sequence without any modification. Different isoforms can be distinguished, for example, by electrophoresis, such as SDS-electrophoresis, and/or isoelectric focusing which is preferred according to the present invention.

Isoforms differing in protein length can be, for example, N-terminally and/or C-terminally extended and/or shortened when compared with the corresponding unmodified protein. For example, a mixture of APG101 isoforms according to the invention can comprise APG101 in unmodified form as well as N-terminally and/or C-terminally extended and/or shortened variants thereof.

Thus, according to a preferred embodiment, the mixture according to the invention comprises N-terminally and/or C-terminally shortened variants of APG101.

Thus, according to a preferred embodiment, the mixture according to the invention comprises N-terminally and/or C-terminally shortened variants of APG101.

In particular, preferred is a mixture of fusion protein isoforms comprising N-terminally shortened fusion proteins.

The shortened fusion proteins can comprise a sequence SEQ ID NO: 1 N-terminally truncated by 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 35, 40, 45 and/or 50 amino acids. Preferred shortened fusion proteins have SEQ ID NO: 1 N-terminally truncated by 16, 20, or 25 amino acids.

Such N-terminally shortened fusion proteins may in terms of the present invention also be named and comprise −1, −2, −3, −4, −5, −6, −7, −8, −9, −10, −11, −12, −13, −14, −15, −16, −17, −18, −19, −20, −21, −22, −23, −24, −25, −26, −27, −28, −29, −30, −35, −40, −45 and/or −50 N-terminally shortened variants of unmodified APG101. Particularly preferred are −17, −21 and/or −26 N-terminally shortened variants. The numbering refers to the APG101 protein including signal sequence according to SEQ ID NO: 1, wherein the number refers to the first amino acid in the N-terminally truncated APG101.

This means a shortened fusion protein having SEQ ID NO: 1 N-terminally truncated by 16 amino acids corresponds to a APG101 variant designated −17 in results in a protein having amino acids 17-400 of SEQ ID NO:1, N-terminally truncated by 20 amino acids (amino acids 21-400 of SEQ ID NO:1) corresponds to −21 and N-terminally truncated by 25 amino acids corresponds to −26 (amino acids 26-400 of SEQ ID NO:1).

An example for a C-terminal shortening of APG101 isoforms is C-terminal Lys-clipping.

According to a preferred embodiment of the present invention the mixture of fusion proteins of the composition according to the present invention preferably comprises 50 mol-% unmodified APG101 in relation to modified isoforms, more preferably 40 mol-% unmodified APG101, more preferably 30 mol-% unmodified APG101, more preferably 20, more preferably 10 mol-% unmodified APG101, more preferably 5 mol-% unmodified APG101 and even more preferably 3 mol-% unmodified APG101 and most preferably 1 mol-% and/or less unmodified APG101. Most preferred is an embodiment comprising a mixture of fusion protein isoforms that does not comprise any unmodified APG101.

As outlined above, isoforms can also differ by amino acid substitution, amino acid deletion and/or addition of amino acids. Such a substitution and/or deletion may comprise one or more amino acids. However, the substitution of a single amino acid is preferred according to this embodiment.

Isoforms according to the invention can also differ with regard to post-translational modification. Post-translational modification according to the present invention may involve, without being limited thereto, the addition of hydrophobic groups, in particular for membrane localisation such as myristoylation, palmitoylation, isoprenylation or glypiation, the addition of cofactors for enhanced enzymatic activity such as lipoyation, the addition of smaller chemical groups such as acylation, formylation, alkylation, methylation, amidation at the C-terminus, amino acid addition, γ-carboxylation, glycosylation, hydroxylation, oxidation, glyciation, biotinylation and/or pegylation.

According to the present invention the addition of sialic acids, Fc-based glycosylation, in particular Fc-based N-terminal glycosylation, and/or pyro-Glu-modification are preferred embodiments of post-translational modification.

According to a preferred embodiment the fusion proteins comprised by the composition of the invention comprise high amounts of sialic acids. According to the present invention the content of sialic acid is preferably from about 4.0 to 7.0 mol NeuAc/mol APG101, more preferably from 4.5 to 6.0 mol NeuAc/mol APG101 and most preferably about 5.0 mol NeuAc/mol APG101. As used herein, sialic acids refer N- or O-substituted derivatives of neuraminic acid. A preferred sialic acid is N-acetylneuraminic acid (NeuAc). The amino group generally bears either an acetyl or glycolyl group but other modifications have been described. The hydroxyl substituents may vary considerably. Preferred hydroxyl substituents are acetyl, lactyl, methyl, sulfate and/or phosphate groups. The addition of sialic acid results generally in more anionic proteins. The resulting negative charge gives this modification the ability to change a protein's surface charge and binding ability. High amounts of sialic acid lead to better serum stability and thus, improved pharmacokinetics and lower immunogenicity. The high degree of sialylation of APG101 isoforms of the present invention could be explained by the high amount of diantennary structure. It has to be regarded as highly surprising that the APG101 isoforms in the composition of the invention obtained by the inventive method show such a high grade of sialic acid addition.

According to the present invention, glycosylation designates a reaction in which a carbohydrate is attached to a functional group of a fusion protein, functional fragment thereof as defined herein. In particular, it relates to the addition of a carbohydrate to APG101 or an isoform thereof. The carbohydrate may be added, for example, by N-linkage or O-linkage. N-linked carbohydrates are attached to a nitrogen of asparagine or arginine site chains. O-linked carbohydrates are attached to the hydroxy oxygen of serine, threonine, tyrosine, hydroxylysine or hydroxyproline side chains. According to the present invention, N-linkage, in particular Fc-based N-terminal glycosylation is preferred. Particularly preferred N-linked glycosylation sites are located at positions N118, N136 and/or N250 of APG101 (SEQ ID NO: 1).

Fucosylation according to the present invention relates to the adding of fucose sugar units to a molecule. With regard to the present invention such an addition of a fucose sugar unit to the fusion protein, and in particular to APG101, represents an especially preferred type of glycosylation. A high portion of fucosylated forms leads to a reduced antibody-dependent cellular cytotoxicity (ADCC). Thus, the mixture of fusion protein isoforms is characterized by reduced ADCC, which is beneficial for pharmaceutical and diagnostic applications.

Of course, beside the first and second domain as defined herein, the fusion proteins according to the invention may comprise further domains such as further targeting domains, e.g. single chain antibodies or fragments thereof and/or signal domains. According to a further embodiment, the fusion protein used according to the invention may comprise an N-terminal signal sequence, which allows secretion from a host cell after recombinant expression. The signal sequence may be a signal sequence which is homologous to the first domain of the fusion protein. Alternatively, the signal sequence may also be a heterologous signal sequence. In a different embodiment the fusion protein is free from an additional N-terminal sequence, such as a signal peptide.

The composition according to the present invention may comprise N-terminally blocked fusion proteins, which provide a higher stability with regard to N-terminal degradation by proteases, as well as fusion proteins having a free N-terminus, which provides a higher stability with regard to N-terminal degradation by proteases.

Modifications blocking the N-terminus of protein are known to a person skilled in the art. However, a preferred post-translational modification according to the present invention blocking the N-terminus is the pyro-Glu-modification. Pyro-Glu is also termed pyrrolidone carboxylic acid. Pyro-Glu-modification according to the present invention relates to the modification of an N-terminal glutamine by cyclisation of the glutamine via condensation of the α-amino group with a side chain carboxyl group. Modified proteins show an increased half-life. Such a modification can also occur at a glutamate residue. Particularly preferred is a pyro-Glu-modification, i.e. a pyrrolidone carboxylic acid, with regard to the N-terminally shortened fusion protein −26.

In a preferred embodiment of the present application the composition according to the present invention comprises 80-99 mol-% N-terminally blocked fusion proteins and/or 1-20 mol-% fusion proteins having a free N-terminus.

According to a further preferred embodiment the composition comprises 0.0 to 5.0 mol-%, more preferably 0.0 to 3.0 mol-% and even more preferably 0.0 to 1.0 mol-%, of fusion protein high molecular weight forms such as aggregates. In a preferred embodiment the composition according to the present invention does not comprise any aggregates of fusion protein isoforms, in particular no dimers or aggregates of APG101. Dimers or aggregates are generally undesired because they have a negative effect on solubility.

Figure 7:
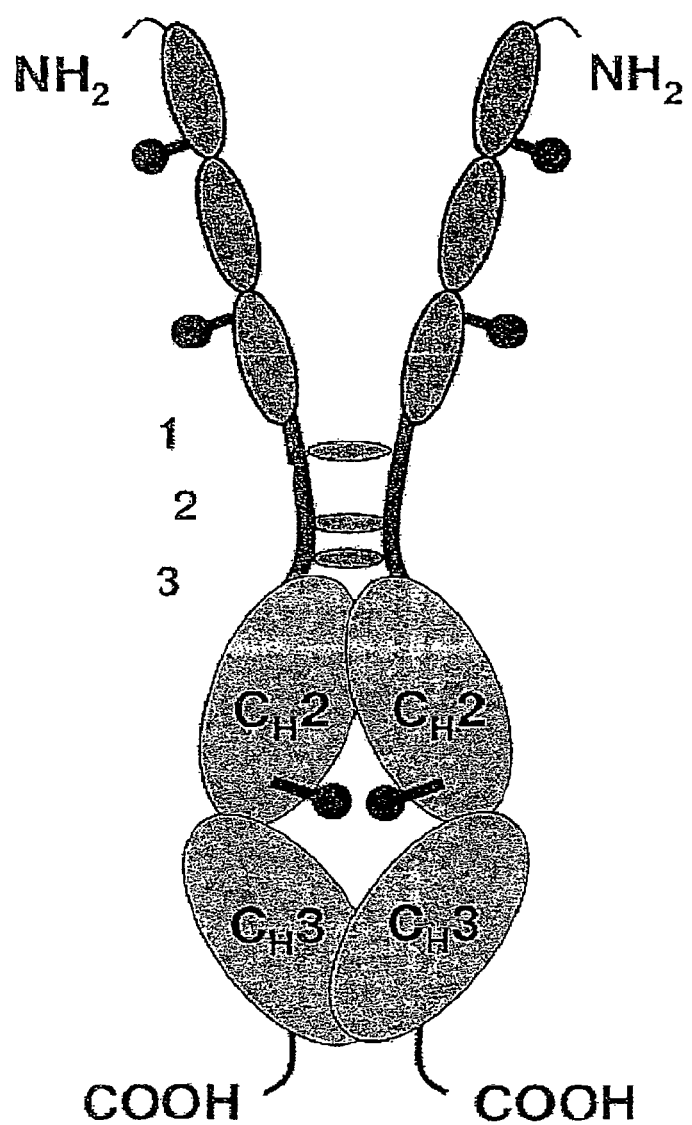
FIG. 7: Functional APG101 molecule.

The functional form of APG101 comprises two fusion proteins, as described herein, coupled by disulfide bridges at the hinge region at positions 179 or/and 182 with reference SEQ ID NO:1 of the two molecules (see FIG. 7). The disulfide bridge may also be formed at position 173 with reference to SEQ ID NO:1 of the two molecules, resulting in an improved stability. If the disulfide bridge at position 173 with reference to SEQ ID NO:1 is not required, the Cys residue at this position can be replaced by another amino acid, or can be deleted.

In a preferred embodiment the mixture according to the present invention is provided by the method according to the present invention described herein.

According to the invention, the mixture of fusion protein isoforms distributes within a pI range of about 4.0 to about 8.5. In a further embodiment the pI range of the mixture of fusion protein isoforms comprised by the composition according to the invention is about 4.5 to about 7.8, more preferably about 5.0 to about 7.5.

The isoelectric point (pI) is defined by the pH-value at which a particular molecule or surface carries no electrical charge. Depending on the pH range of the surrounding medium the amino acids of a protein may carry different positive or negative charges. The sum of all charges of a protein is zero at a specific pH range, its isoelectric point, i.e. The pI value. If a protein molecule in an electric field reaches a point of the medium having this pH value, its electrophoretic mobility diminishes and it remains at this site. A person skilled in the art is familiar with methods for determining the pI value of a given protein, such as isoelectric focusing. The technique is capable of extremely high resolution. Proteins differing by a single charge can be separated and/or fractionated.

The composition according to the present invention described herein may be used for pharmaceutical, diagnostic and/or research applications. It may be applied in human medicine as well as veterinary medicine.

Another aspect of the present invention relates to a formulation comprising a composition according to the invention.

According to a preferred embodiment the formulation comprises
(a) phosphate, preferably about 20 mM to about 100 mM phosphate, more preferably about 30 mM to about 70 mM phosphate, even more preferably about 40 mM to about 60 mM phosphate, most preferred about 50 mM phosphate,
(b) a viscosity enhancing agent, preferably about 0.1-10 weight-% viscosity enhancing agent, more preferably 1 to 8 weight-% viscosity enhancing agent, more preferably about 3 weight-% to about 7 weight-% viscosity enhancing agent, even more preferred about 6 weight-% to about 7 weight-% viscosity enhancing agent, and most preferred about 5 weight-% viscosity enhancing agent, and (c) has a pH value in the range of 4-8.

Viscosity enhancing or increasing agents are well-known to a person skilled in the art and comprise alginic acid, carboxymethyl cellulose, dextrin, gelatin, guar gum, hydroxyethyl cellulose, magnesium aluminum silicate, polyvinyl alcohol, polyethylene oxide, silicon dioxide, starch, xanthan gum, etc. However, a viscosity enhancing agent which is especially preferred according to the present invention is sorbitol.

Surprisingly, the composition of the invention provided in that type of formulation is very stable and does not tend to form aggregates. Moreover, it was possible to provide high protein concentrations, e.g. about 20 mg/ml in stable form.

The composition and/or formulation according to the invention can be administered to a subject in need thereof, particularly a human patient, in a sufficient dose for the treatment of the specific conditions by suitable means. For example, the composition and/or formulation according to the invention may be formulated as a pharmaceutical composition together with pharmaceutically acceptable carriers, diluents and/or adjuvants. Therapeutic efficiency and toxicity may be determined according to standard protocols. The pharmaceutical composition may be administered systemically, e.g. intraperitoneally, intramuscularly, or intravenously or locally such as intranasally, subcutaneously or intrathecally. The dose of the composition and/or formulation administered will, of course, be dependent on the subject to be treated and on the condition of the subject such as the subject's weight, the subject's age and the type and severity of the disease or injury to be treated, the manner of administration and the judgement of the prescribing physician. For example, a daily dose of 0.001 to 100 mg/kg is suitable.

Another aspect of the present invention relates to a pharmaceutical composition or formulation comprising the composition or formulation according to the invention, which contains at least one further active agent. Which further active agent is used depends on the indication to be treated. For example, cytotoxic agents such as doxorubicin, cisplatin or carboplatin, cytokines or other anti-neoplastic agents may be used in the treatment of cancer.

The formulation and/or composition according to the invention may further comprise pharmaceutically acceptable carriers, diluents, and/or adjuvants. The term "carrier" when used herein includes carriers, excipients and/or stabilizers that are non-toxic to the cell or mammal being exposed thereto at the dosages and concentrations employed. Often the physiologically acceptable carriers an aqueous pH buffered solutions or liposomes. Examples of physiologically acceptable carriers include buffers such as phosphate, citrate and other organic acids (however, with regard to the formulation of the present invention, a phosphate buffer is preferred); anti-oxidants including ascorbic acid, low molecular weight (less than about 10 residues) polypeptides; proteins such as serum albumin, gelatine or immunoglobulins; hydrophilic polymers such as polyvinyl pyrrolidone; amino acids such as glycine, glutamine, asparagine, arginine or lysine; monosaccharides, disaccharides, and other carbohydrates including glucose, mannose or dextrins, gelating agents such as EDTA, sugar, alcohols such as mannitol or sorbitol; salt-forming counterions such as sodium; and/or non-ionic surfactants such as TWEEN, polyethylene or polyethylene glycol.

According to a preferred embodiment the composition and/or formulation according to the invention can be used to inhibit the CD95 signalling pathway, in particular the extrinsic apoptotic pathway triggered by CD95L, i.e. The CD95 receptor ligand. In particular, the composition can be used in the prophylaxis and/or treatment of disorders selected from autoimmune disorders, AIDS, heart disorders, e.g. myocardial infarction, graft-versus-host disorders, transplant rejection, brain damage, e.g. stroke, spinal cord injuries, sepsis, hepatitis, disorders associated with inflammation, ischemic reperfusion injury and renal disorders. Of course, the composition and/or formulation described herein may be used for the treatment of cancers, preferably solid cancers, e.g., brain cancers, e.g., glioblastomas. Alternatively, the cancer to be treated may be a cancer of lymphoid or myeloid origin.

Another aspect of the present invention relates to a method for producing a composition according to the invention. According to a preferred embodiment the method comprises the steps (a) production of a composition as provided by the present invention by a feed batch production process, providing a cell harvest and (b) isolation of the composition of the present invention from the cell harvest.

One advantage of the method of the present invention compared to the methods known from the prior art is its high yield.

Step (a), i.e. The "method for producing a composition according to the present invention by a feed-batch production process providing a cell harvest" will also be designated as "upstream process (USP)" in the following. The method according to step (a) of the present invention is also referred to as "inventive USP". FIG. 1 shows a comparison of the upstream process according to the prior art and a preferred embodiment of the upstream process of the present invention.

Step (b), i.e. "isolation of the composition of the present invention from the cell harvest" will also be designated as "downstream process (DSP)" in the following.

Preferably, step (a) comprises a series of cultivation steps of a given master cell batch until relevant harvest parameters are reached followed by sedimentation and filtration of fusion protein, preferably containing supernatant. In a preferred embodiment of the present invention the process steps of the upstream process may be summarized as a series comprising the following steps.

Thawing,
subcultivation,
50 l bioreactor,
200 l bioreactor,
1000 l bioreactor,
sedimentation,
depth and
0.2 μm filtration.

Of course, carrying out the cultivation steps from subcultivation to the 1000 l bioreactor is only one way of carrying out the invention. For example, the cultivation steps may be carried out in bioreactors with varying sizes as well. Of course, during the series of subcultivation steps, the person skilled in the art can determine suitable parameters like temperature, growth time, media, etc. The crucial factor is to achieve relevant harvest parameters, which may be a titer, the cell density, with the titer being preferably within a range of 0.5 g/l to 5 g/l, more preferably 1 g/l to 3 g/l, more preferably 1.5 g/l to 5 g/l and most preferably being 1.8 g/l to 2 g/l. Examples for preferred values of cell density are about $1 \times 10^6$ to $1 \times 10^8$ cells/ml, preferably about $1 \times 10^7$ cells/ ml. In an especially preferred embodiment of the present invention the titer is about 1.8 g/l to about 2 g/l and the cell density is about 1×10⁷ cells/ml.

The method according to the present invention is preferably carried out in a pepton-containing basal medium and a chemically defined medium.

Step (b) may comprise capture chromatography, virus inactivation, a series of anion and/or cation chromatography, virus filtration and/or adjustment to a desired final protein concentration.

The downstream process of purifying a composition comprising APG101 isoforms obtained by step (a) according to step (b) defined above comprises chromatography steps, a virus inactivation step, an ultrafiltration step, a diafiltration step and a virus filtration step. According to a preferred embodiment, this downstream process comprises three different chromatographic steps. The first chromatography step is carried out with a resin to capture the target protein and/or to remove process-related impurities (e.g., HCPs, DNA) and or to reduce the volume of the product-containing fraction. A corresponding resin can be selected by the person skilled in the art. An example of a resin is Mab Select SuRE, which is also a preferred embodiment according to the invention.

After this first chromatography step a virus inactivation step follows. Preferably, this virus inactivation step is performed under acidic conditions (e.g., pH 3.5±0.2) followed by a conditioning of the inactivation pool or at a less acidic pH value such as pH 5.0. The buffer matrix for virus inactivation and subsequent pH 5.0 adjustment may be solely based on 20 nM Na-citrate buffer.

After this virus inactivation step chromatography, an ion exchange step is carried out in order to reduce process-related impurities such as DNA. According to the present invention an anion exchange chromatography (AIEX) step is preferred, particular in a flow-through mode. The target protein passes the AIEX column, whereas DNA binds to the resin. Preferably, the AIEX flow-through pool is subsequently processed without any conditioning using a further column-based step. This optional further step contributes to the overall reduction of virus contamination and residual HCP, DNA and bleached protein-A ligand. According to a preferred embodiment a mix-mode resin capto-MMC operated column in bind/eluate mode is used.

The eluate is passed through a virus filter (VF) and applied to an ultra-diafiltration step (UF/DF) subsequently. According to the invention a specific volumetric load of ≤100 l/m² can be obtained on the virus filtration step. Preferably, a membrane with about a 30 kD cut-off is used. Of course, single purification steps described above can be replaced by steps known to the person skilled in the art achieving the same or a comparable effect.

Finally, the UF/DF retentate is formulated and the concentration of the APG101 composition according to the present invention is adjusted to the desired protein concentration such as 20±2 mg/ml.

Figure 2:
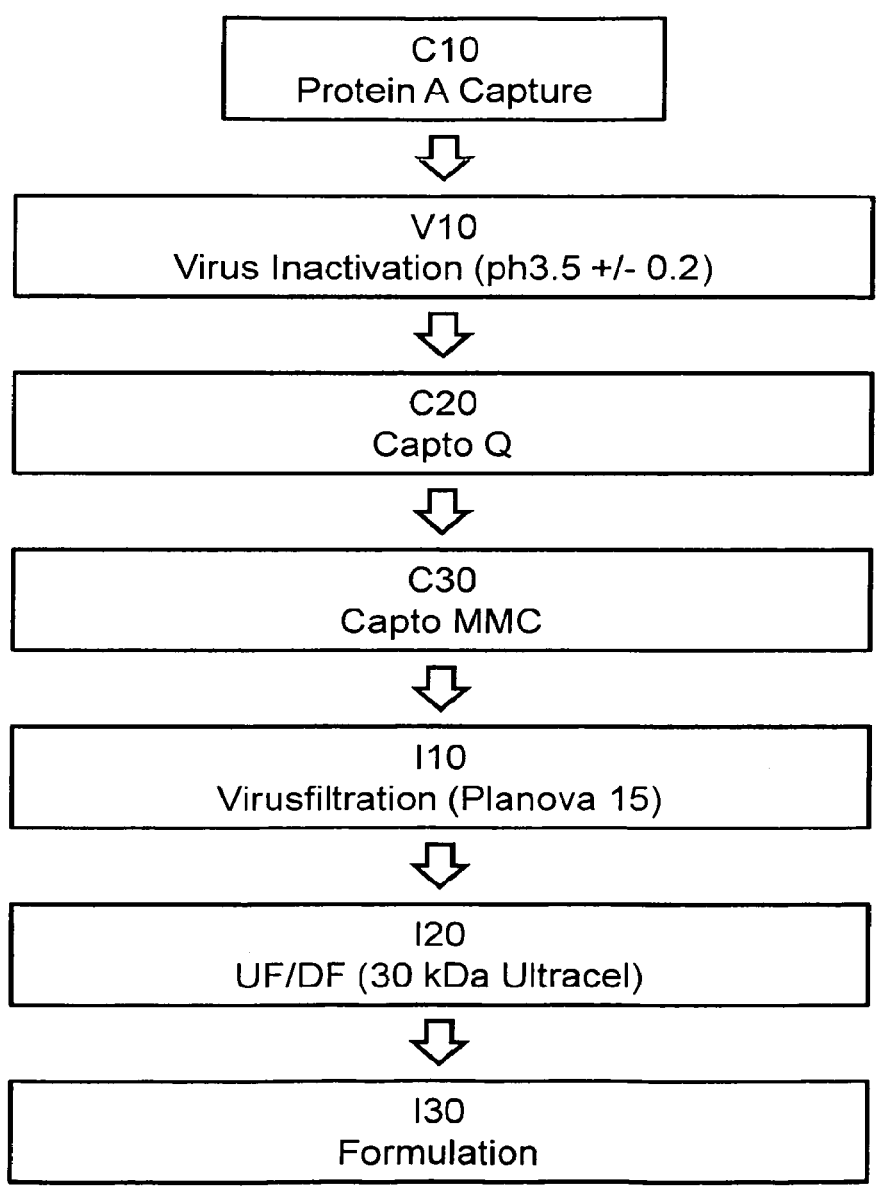
FIG. 2: Flow scheme showing a preferred embodiment of the downstream process of the invention
Figure 3:
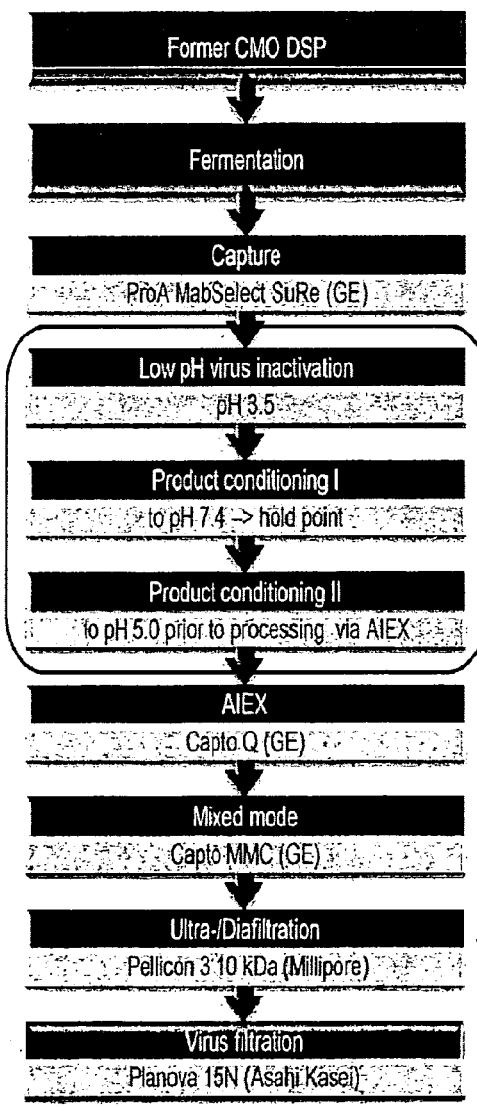
FIG. 3: Comparison of the inventive downstream process with a non-inventive downstream process
Figure 3:
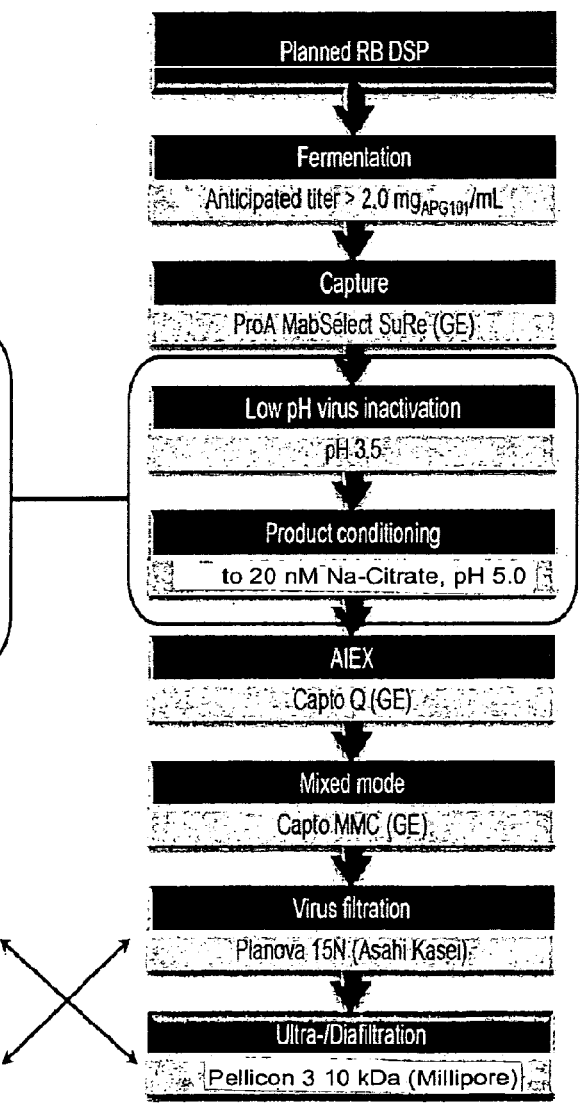

FIG. 2 illustrates the flow scheme of a preferred embodiment of a downstream process according to the present invention. As can be taken from FIG. 3 the inventive downstream process is characterized by a number of advantages over downstream processes known from the prior art. For example, after virus inactivation no holding step at a neutral pH value is required. With regard to the virus filtration step, a volumetric load ≤100 l/m² is possible compared to 37 g/m² known in prior processes. Further, using the formulation buffer of the present invention high protein concentrations such as 20 mg/ml can be reached compared to 10 mg/ml in PBS.

The method for producing a composition according to the present invention, which is described herein, results in APG101 isoforms in pI range of 4.0 to 8.5. A composition provided this way only contains very small amounts of unwanted higher molecular weight forms such as dimers or aggregates. APG101 isoforms provided this way are characterized by high amounts of sialic acid content as well as Fc-based N-terminal glycosylation comprising high amounts of fucosylated forms.

Another aspect of the present invention is a fusion protein comprising at least an extracellular CD95 domain or a functional fragment thereof and at least a Fc domain or a functional fragment thereof.

The extracellular CD95 domain can be a human extracellular CD95 domain. The extracellular CD95 domain can comprise SEQ ID NO:7 and sequences having at least 70%, at least 80%, at least 90%, at least 95%, or at least 97% identity to SEQ ID NO:7.

In the fusion protein according to the present invention, disulfide bridges can be present in the CD95 domain or the functional fragment thereof linking positions 34 and 48, 38 to 57, 60 and 76, 79 and 94, 82 and 102, 104 and 118, 110 and 115, 121 and 132, or/and 124 and 140 with reference to SEQ ID NO:7. A preferred fusion protein comprises a disulfide bridge at position 110 to 115 with reference to SEQ ID NO:7. A disulfide bridge can also be present in the Fc domain or a functional fragment thereof linking position 43 and 103 or/and position 149 and 207 with reference to SEQ ID NO:8.

It is contemplated that a reference to a specific position of SEQ ID NO:7 or SEQ ID NO:8 includes a reference to corresponding positions of SEQ ID NO:1, SEQ ID NO:2, SEQ ID NO:3, SEQ ID NO:4, SEQ ID NO:5, SEQ ID NO:6, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, or SEQ ID NO:19, if applicable. For example, the disulfide bridge at position 104 and 118 with reference to SEQ ID NO:7 corresponds to a disulfide bridge at position 129 to 143 with reference to SEQ ID NO:1.

In the present invention, it has surprisingly been found that in the fusion protein, the N terminal truncation of the extracellular CD95 domain of up to 33 amino acids in SEQ ID NO:7 does not reduce stability compared with full-length APG101. For example, fusions proteins of SEQ ID NO:3, SEQ ID NO:4, SEQ ID NO:5, and SEQ ID NO:6 provide a stability which is at least the stability of the full-length APG101 (Example 2). Another aspect of the present invention is thus a fusion protein comprising a functional fragment of the extracellular CD95 domain of SEQ ID NO:7 being truncated until position 33. In the fusion protein, the functional fragment of the extracellular CD95 domain can comprise SEQ ID NO:7 truncated by up to 33 N terminally located amino acids. In the fusion protein of the present invention, the functional fragment of the extracellular CD95 domain can comprise an amino acid sequence wherein 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, or 33 N terminal amino acids are truncated in SEQ ID NO:7.

In a preferred aspect, 13 N terminal amino acids are truncated in the extracellular CD95 domain (SEQ ID NO:3).

In another preferred aspect, 14 N terminal amino acids are truncated in the extracellular CD95 domain (SEQ ID NO:4).

In yet another preferred aspect, 29 N terminal amino acids are truncated in the extracellular CD95 domain (SEQ ID NO:5).

In yet another preferred aspect, 31 N terminal amino acids are truncated in the extracellular CD95 domain (SEQ ID NO:6).

In a further aspect, the fusion protein of the present invention can comprise a functional fragment comprising an amino acid sequence selected from the group consisting of SEQ ID NO:9, SEQ ID NO:10, SEQ ID NO:11, SEQ ID NO:12, and sequences having at least 70%, at least 80%, at least 90%, at least 95%, or at least 97% identity to SEQ ID NO:9, SEQ ID NO:10, SEQ ID NO:11, or SEQ ID NO:12. In particular, the fusion protein can comprise a functional fragment of the extracellular CD95 domain comprising an amino acid sequence selected from the group consisting of SEQ ID NO:9, SEQ ID NO:10, SEQ ID NO:11, and SEQ ID NO:12.

In the fusion protein according to the present invention the at least a Fc domain can be a human Fc domain. Suitable Fc domains and Fc fragments are described herein. In particular the at least a Fc domain can comprise an amino acid sequence selected from the group consisting of SEQ ID NO:8 and sequences having at least 70%, at least 80%, at least 90%, at least 95%, or at least 97% identity to SEQ ID NO:8.

The fusion protein according to the present invention can be free of a signal peptide, as the signal peptide present in the immature expression product will be cleaved off during maturation.

In another aspect, the fusion protein according to the present invention can comprise an N terminally located signal peptide.

The signal peptide can be a naturally occurring CD95 signal peptide, as, for example a signal peptide comprising SEQ ID NO:14. The signal peptide can be a modified natural signal peptide, for example a signal peptide comprising SEQ ID NO:13. SEQ ID NO:13 corresponds to positions 1 to 25 of SEQ ID NO:1. SEQ ID NO:13 corresponds to SEQ ID NO:14, except position 2 (Leu in SEQ ID NO:14, Val in SEQ ID NO:13).

In a preferred aspect, in the fusion protein of the present invention, the N-terminally located signal peptide is an artificial signal peptide. More preferably, the signal peptide comprises SEQ ID NO:2 or a sequence having at least 90%, or at least 95% identity to SEQ ID NO:2.

In the fusion protein according to the present invention, the extracellular CD95 domain or the functional fragment thereof can be located N-terminally of the at least a Fc domain or the functional fragment thereof. The signal peptide, if present, can be directly fused to the extracellular CD 95 domain or the functional fragment thereof.

In the fusion protein according to the present invention the extracellular CD95 domain or the functional fragment thereof can be directly fused to an Fc domain or the functional fragment thereof. An overlap of one amino acid (for example, Ser at position 172 of SEQ ID NO:1 and at corresponding positions of other sequences disclosed herein) can be present.

In another aspect of the present invention, the fusion protein is APG101, or a polypeptide having at least 70%, at least 80%, at least 90%, at least 95%, or at least 97% identity to APG101 and/or a functional fragment of APG101. The fusion protein of the present invention can comprise SEQ ID NO:1, or a sequence having at least 70%, at least 80%, at least 90%, at least 95%, or at least 97% identity to SEQ ID NO:1. The fusion protein of the present invention can also comprise SEQ ID NO:15, or a sequence having at least 70%, at least 80%, at least 90%, at least 95%, or at least 97% identity to SEQ ID NO:15.

In yet another aspect of the present invention, the fusion protein can comprise a sequence selected from the group consisting of SEQ ID NO:3, SEQ ID NO:4, SEQ ID NO:5, SEQ ID NO:6, and sequences having at least 70%, at least 80%, at least 90%, at least 95%, or at least 97% identity to SEQ ID NO:3, SEQ ID NO:4, SEQ ID NO:5, or SEQ ID NO:6. SEQ ID NOs: 3-6 provide a sequence including a signal peptide of SEQ ID NO:2.

In yet another aspect of the present invention, the fusion protein can comprise a sequence selected from the group consisting of SEQ ID NO:16, SEQ ID NO:17, SEQ ID NO:18, SEQ ID NO:19, and sequences having at least 70%, at least 80%, at least 90%, at least 95%, or at least 97% identity to SEQ ID NO:16, SEQ ID NO:17, SEQ ID NO:18, or SEQ ID NO:19. SEQ ID NOs: 16-19 are free of a signal peptide.

In another aspect of the present invention, in the fusion protein, the at least a Fc domain or a functional fragment thereof can provide a pI in the range of 4.0-8.5, preferably in the range of 4.5-7.8, more preferably 5.0-7.5, as described herein in the context of the mixture of fusion proteins.

In one aspect of the present invention, the fusion protein of the present invention is not glycosylated in the CH2 domain of the Fc domain or the functional fragment thereof. It is preferred to prevent glycosylation by replacing the Asn residue N250 in SEQ ID NO:1 (or at a corresponding position in another sequence disclosed herein, for example position 79 in SEQ ID NO:8) by serine.

In yet another aspect of the present invention, the fusion protein can comprise high amounts of sialic acids, as described herein in the context of the mixture of fusion proteins.

In yet another aspect of the present invention, in the fusion protein, the Fc based N-linked glycosylation is characterized by high amounts of fucosylated forms, as described herein in the context of the mixture of fusion proteins.

In yet another aspect of the present invention, the fusion protein comprises N-terminally blocked fusion proteins, such as fusion proteins blocked by pyro-Glu modification and/or comprising fusion proteins having a free N-terminus, as described herein in the context of the mixture of fusion proteins. The fusion protein can comprise 80-99 mol-% N-terminally blocked fusion proteins and/or 1-20 mol-% fusion proteins having a free N-terminus, as described herein in the context of the mixture of fusion proteins.

The fusion protein of the present invention can be an isolated fusion protein.

Yet another aspect of the present invention is a nucleic acid molecule encoding the fusion protein of the present invention. Said nucleic acid preferably is in operative linkage to at least one expression control sequence suitable for expression in a host cell as described herein. The skilled person knows suitable expression control sequences, for example promoters, enhancers, terminators etc.

Yet another aspect of the present invention is a host cell comprising a nucleic acid molecule of the present invention. The host cell can be an eukaryotic cell, in particular a mammalian cell, more particular a human cell. Preferred cell lines include HEK293 and CHO. Most preferred is a CHO suspension cell, which can be pre-adapted to a chemically defined culture medium.

Yet another aspect of the present invention is a formulation comprising a fusion protein according to the present invention, or/and a nucleic acid molecule according to the present invention. The formulation is in particular a pharmaceutical composition optionally comprising a carrier, diluent or/and auxiliary substance, as described herein. The formulation can be used in the treatment of a disease or condition, as described herein.

The formulation of the present invention can further comprise:
(a) phosphate, preferably about 20 mM to about 100 mM phosphate, more preferably about 50 mM phosphate,
(b) a viscosity enhancing agent, such as sorbitol, preferably about 0.1-10 weight-% viscosity enhancing agent, more preferably about 5 weight-% viscosity enhancing agent, and/or
(c) having a pH value in the range of 4-8.

Yet another aspect of the present invention is a method for producing a fusion protein according to the present invention, comprising recombinant expression of a nucleic acid molecule encoding the fusion protein, in particular in a host cell as described herein. The skilled person knows suitable methods. The method can comprise the steps
(a) production of a fusion protein according to the present invention by a fed-batch production process providing a cell harvest, and
(b) isolation of the fusion protein according to the present invention from the cell harvest.

In the method for producing a fusion protein step (a) can comprise a series of cultivation steps of a given master cell batch until relevant harvest parameters are reached, followed by cell sedimentation and filtration of fusion protein containing supernatant, and/or step (b) can comprise capture chromatography, virus inactivation, a series of anion and/or cation chromatography, virus filtration and/or adjustment to a desired final protein concentration.

Yet another aspect of the present invention is a polypeptide comprising SEQ ID NO:2 or a sequence having at least 90%, or at least 95% identity to SEQ ID NO:2. SEQ ID NO:2 describes an artificial signal peptide capable of transporting a peptide or protein expressed in a eukaryotic host cell to the cell surface. Preferably, the signal peptide consists of a SEQ ID NO:2. It has surprisingly been found that in the expression of a protein or polypeptide having a Lys, Thr, Asp or Gln in the first position of the mature polypeptide, a signal peptide comprising SEQ ID NO:2 results in a mature peptide precisely cut between the signal peptide and the first amino acid of the mature peptide. In contrast, a signal sequence, as for example in positions 1 to 25 in SEQ ID NO:1, provides variable cleavage behind position 16, 20 or 25 so that a mixture of cleavage products is obtained. In this case, fusion proteins can be obtained having a first amino acid being Arg17, Lys21 or Pyro-Glu26 with reference to SEQ ID NO:1. Any peptide or protein can be expressed in a eukaryotic cell with the aid of the signal peptide comprising SEQ ID NO:2 or a sequence having at least 90%, or at least 95% identity to SEQ ID NO:2. In particular, the polypeptide to be expressed with the aid of a signal peptide comprising SEQ ID NO: 2, or a sequence having at least 90%, or at least 95% identity to SEQ ID NO:2, can be a fusion protein as described herein, for example a fusion protein of any one of SEQ ID NO:3, SEQ ID NO:4, SEQ ID NO:5, SEQ ID NO:6, SEQ ID NO:15, SEQ ID NO:16, SEQ ID NO:17, SEQ ID NO:18, and SEQ ID NO:19.

Yet another aspect is a nucleic acid encoding a polypeptide comprising SEQ ID NO:2, or a sequence having at least 90%, or at least 95% identity to SEQ ID NO:2.

Other aspects of the present invention relate to truncated extracellular CD95 domains, as described herein. Preferred is a truncated extracellular CD95 domain comprising SEQ ID NO: 9, SEQ ID NO:10, SEQ ID NO:11 or SEQ ID NO:12. Further aspects relate to nucleic acids encoding truncated extracellular CD95 domains, as described herein.

SEQ ID NO:1 describes APG101 including a signal peptide.
SEQ ID NO:2 describes an artificial signal peptide.
SEQ ID NO:3 describes a truncated form of APG101 termed APG130, including the artificial signal peptide of SEQ ID NO:2.
SEQ ID NO:4 describes a truncated form of APG101 termed APG131, including the artificial signal peptide of SEQ ID NO:2.
SEQ ID NO:5 describes a truncated form of APG101 termed APG132, including the artificial signal peptide of SEQ ID NO:2.
SEQ ID NO:6 describes a truncated form of APG101 termed APG133, including the artificial signal peptide of SEQ ID NO:2.
SEQ ID NO: 7 describes a human CD95 extracellular domain (positions 26 to 172 of SEQ ID NO:1).
SEQ ID NO: 8 describes a human Fc domain (positions 172 to 400 of SEQ ID NO:1).
SEQ ID NO:9 describes a truncated form of the extracellular domain of human CD95 (positions 21 to 154 of SEQ ID NO:3).
SEQ ID NO:10 describes a truncated form of the extracellular domain of human CD95 (positions 21 to 153 of SEQ ID NO:4).
SEQ ID NO:11 describes a truncated form of the extracellular domain of human CD95 (positions 21 to 138 of SEQ ID NO:5).
SEQ ID NO:12 describes a truncated form of the extracellular domain of human CD95 (positions 21 to 136 of SEQ ID NO:6)
SEQ ID NO:13 describes a modified human CD95 signal peptide (position 1 to 25 of SEQ ID NO:1).
SEQ ID NO:14 describes a human CD95 signal peptide.
SEQ ID NO:15 describes a mature form of APG101 (position 26-400 of SEQ ID NO:1).
SEQ ID NO:16 describes a mature form of APG130 (position 21-382 of SEQ ID NO:3).
SEQ ID NO:17 describes a mature form of APG131 (position 21-381 of SEQ ID NO:4).
SEQ ID NO:18 describes a mature form of APG132 (position 21-366 of SEQ ID NO:5).
SEQ ID NO:19 describes a mature form of APG133 (position 21-364 of SEQ ID NO:6).

EXAMPLE 1

Method for Producing a Composition According to the Invention

The method for providing a composition according to the present invention comprises an upstream process and a downstream process as defined above.
1. Upstream Process
1.1 Batch Definition
The composition comprising APG101 isoforms is produced in a fed-batch cultivation. Two vials of the master cell bank MCB1AGA are thawed. The viability of the third subcultivation has to be >90%, the viable cell count has to be >1.5×106 cells/mL. If both vials fulfill these specifications, the culture with the higher viability is used for the fourth subcultivation and inoculation of the seed reactor. The culture with lower viability will be discarded after third subcultivation. The cell culture is expanded in shake flasks up to ≥4 L total volume before inoculating the first seed bioreactor. As first seed bioreactor a 50 L Xcellerex disposable bioreactor (XDR) is used. The cell culture is cultivated for three days before being transferred into the second seed reactor 200 L XDR. After another 3 days of cultivation, the 1000 L production reactor is inoculated. Harvesting procedure is started at day 13 or earlier, if the viability drops below 61%.

1.2 Cell Line

The utilized Master Cell Bank (MCB) is designated "MCB1AGA".

1.3 Thawing and Subcultivations

Two cryo vials of the MCB are resuscitated consecutively. The following thawing procedure is applied for each vial: The cryo vials are thawed in a beaker with WFI at 36.8° C. (setpoint) until a small ice crystal remains. Cells are then transferred into approx. 10 mL of cooled (at 5±3° C.) growth media (media no. 3001772, purchased from PAA), supplemented with 6 mM L-glutamine (final concentration) and 50 nM MTX (final concentration). To remove residual DMSO, a washing step in cooled (5±3° C.) medium is performed via centrifugation. The cell pellet is resuspended in 50 mL of prewarmed (36.8±1° C.) medium after the centrifugation step. Cell concentration and viability are measured with the Cedex cell counter. This Out-of-Freeze culture is finally incubated in a shaker incubator with a working volume of 50 ml using 250 ml shake flasks.

The first and second subcultures are stability splits performed with a working volume of 120 ml (first subculture) and 150 mL (second subcultures) using 500 ml shake flasks. The third and fourth subcultures are the first expansion phase and performed in 2000 mL shake flasks with a working volume of 800 mL. For these initial four passages, the pre-warmed (at 36.8±1° C.) growth media (media no. 3001772, purchased from PAA), supplemented with 6 mM L-glutamine and 50 nM MTX (final concentrations), is used as cultivation medium.

Measurement of cell concentration and viability is performed prior to each cultivation step using a Cedex cell counter. The next subculture is prepared depending on the cell growth.

At subculture no. 5, the shake flasks are pooled in a 5 L glass bottle. This pool is sampled for cell concentration and viability. Depending on the actual VCC the required cell culture volume is then transferred into a 50 L seed bioreactor.

1.4 Seed Bioreactor (50 L)

The 50 L seed bioreactor is equipped with a bottom-mounted magnetic drive agitator system and 1 mm sparger discs. Prior to inoculation the 50 L bioreactor is filled with approx. 20 L of growth media (media no. 3001772, purchased from PAA) supplemented with 6 mM L-glutamine (final concentration). These parameters apply to the medium pre-conditioning and to the seed train cultivation process.

When the process parameters are stable within their acceptable ranges the inoculum transfer is started. After inoculation the reactor is filled up with medium to a final working volume of 25 L. During cell mass expansion in the 50 L bioreactor no feed addition is applied to the process. The pH is controlled with CO2 via sparger. The oxygen level is controlled by submerse aeration with oxygen on demand. An overlay gas flow of air is applied to the headspace. Submerse aeration with pressurized air with a flow rate of 0.1 L/min, which can be adapted for adjusting pCO2, is performed. The expected cultivation time in the seed bioreactor is 3 days before inoculation of a 200 L seed bioreactor.

1.5 Seed Bioreactor (200 L)

The 200 L seed bioreactor is equipped with a bottom-mounted magnetic drive agitator system and 1 mm sparger discs. Prior to inoculation the 200 L bioreactor is filled with approx. 100 L of growth media (media no. 3001772, purchased from PAA) supplemented with 6 mM L-glutamine (final concentration). These parameters apply to the medium pre-conditioning and to the seed train cultivation process.

When the process parameters are stable within their acceptable ranges the inoculum transfer is started. After inoculation, medium is added to a final working volume of 120 L. During cell mass expansion in the 200 L bioreactor no feed addition is applied to the process. The pH is corrected with $CO_2$ gas. The oxygen level is controlled by submerse aeration with oxygen on demand. An overlay gas flow of air is applied to the headspace. Submerse aeration with pressurized air with a flow rate of 0.4 L/min, which can be adapted for adjusting $pCO_2$, is performed. The expected cultivation time in the seed bioreactor is 3 days before cells are transferred into a 1000 L production bioreactor.

1.6 Fed-Batch Production Process

The production process of a composition comprising APG101 isoforms is a fed-batch cultivation. A 1000 L production bioreactor is equipped with a bottom-mounted magnetic drive agitator system and 1 mm sparger discs. Prior to inoculation the 1000 L bioreactor is filled with approx. 580 L growth medium (media no. 3001829, purchased from Becton Dickinson) and supplemented with 6 mM L-glutamine (final concentration, calculated on the final starting volume of 720 L). When the process parameters are within their acceptable ranges the inoculum transfer from the seed bioreactor to the production bioreactor is started. The target cell concentration after inoculation in the production bioreactor is 0.3*106 viable cells/mL in a total volume of 720 L. The required volume of the seed bioreactor cell culture is transferred to the production reactor, which is then filled up with growth medium (media no. 3001829, purchased from Becton Dickinson) until the starting volume of 720 L is reached. The cell culture is fed with Feedmedium A (PM30728) starting at day 3, and Glucose Feedmedium B (PM30729).

Daily feeding is started with Feed B separately, Feed A and Glucose can be fed simultaneously.

Feedmedium B:

Bolus feed starts at day 3 after sampling.

Feeding rate day 3-6:5.184 g/L/d (calculated on start volume of 720 L)

Feeding rate day 7-12:2.592 g/L/d (calculated on start volume of 720 L)

Feedmedium A:

Bolus feed starts at day 3 after sampling.

Feeding rate day 3-5:43.2 g/L/d (calculated on start volume of 720 L)

Feeding rate day 6-12:21.6 g/L/d (calculated on start volume of 720 L)

D-Glucose Feed: Glucose is added when the actual D-glucose concentration is <5 g/L starting at day 7. The concentration of D-glucose is adjusted to 5 g/L by adding the required amounts of D-Glucose feed.

The oxygen level is controlled by application of a oxygen controller cascade with 3 priorities: Priority 1 consists of a flow of process air on demand until an gas flow of 10 L/min is reached. Then the agitation (priority 2) is increased continuously until a stirring speed of 100 rpm is reached. The third priority consists of submerse sparging O2 on demand.

An air overlay flow is applied to the headspace.

The pH is controlled with $CO_2$. If necessary 1 M $Na_2CO_3$ is prepared to be added if necessary. Formation of foam is observed regularly and antifoam is added if necessary.

The harvesting procedure is started at cultivation day 13, or earlier if the viability drops below <61% (Cedex). First step of the procedure is the sedimentation of cells, where the cell broth is cooled down to 10±5° C. When the temperature is below 20° C., stirrer, aeration and pH control are switched off. After a minimum of 12 h of sedimentation the clarification step is started. Supernatant is clarified by a two step depth filtration and 0.2 μm filtration.

1.7 Sedimentation

The harvesting procedure is started by a sedimentation step. Culture broth is cooled down to finally 10±5° C. When the temperature is <20° C., agitation, $pO_2$ and pH-control are inactivated. After min. 12 h and max. 22 h hours of sedimentation, depth filtration is started.

1.8 Filtration

The depth filtration is performed with the Stax™ Disposable Depth Filter Systems from Pall, loading 7× PDK5 and 2× PDD1 depth filters. The clarification is followed by a 0.2 μm filtration. The depth filters are flushed with approx. 900 L PBS at a flux rate of ≤100 L/m2/h. The residual liquid is blown out of the system with air. Filtration process is run with a pump flow rate of ≤3.5 L/min and a maximum pressure of 1.0 bar. To increase the product recovery, the filters are rinsed afterwards with approx. 60 L PBS pH 7.25 and blown out with pressurized air at a maximum pressure at 0.8 bar. Filtrated harvest is transferred directly through the wall duct into the GD suite, collected in a 1000 L Mixtainer and stored at room temperature.

2. Downstream Process

For illustration purposes a description of the individual purification steps during the downstream process will be given in the following.

2.1 Protein A Capture (C10)

The filtration material from above was transferred depth filtrated (0.2 μm) and tempered to 5±3° C. Prior to processing the harvest was split in four equal aliquots and stored at room temperature over night to achieve final process temperature of 21 ±3° C. The processing of harvest was carried out without any further conditioning on in four cycles.

The elution was induced via a low pH step. The UV280 profiles of the four cycles were highly congruent and show the expected shape including the typical single peak within the elution step.

The yields of the Protein A runs varied between 94 to 98%. Hence, the product recovery of the Protein A runs was in the expected range. Furthermore, all recoveries were comparable with each other and confirmed the data acquired during process transfer and adaptation.

2.2 Virus Inactivation (V10)

Immediately after collecting the Protein A eluate a fixed volume addition (specification: pH 3.5±0.2) was executed with 20 mM citric acid within 5 min to inactivate enveloped viruses. The obtained virus inactivation solutions were incubated separately for 75±15 min at room temperature (21±3° C.). Finally, the pH of the inactivation solutions was adjusted to pH5.0±0.2 via addition of a fixed volume of 20 mM Na3-Citrate to stop virus inactivation. The entire conditioning schemes were as follows:

Subsequently, the conditioned virus inactivation solutions were filtered via a 0.22 μm filter (Sartobran P) to separate potentially formed precipitates and to inhibit microbial growth in the process solution. Each conditioned virus inactivation batch was stored at 21±3° C. and finally pooled prior to processing via the AIEX (C20) step.

2.3 AIEX (C20)—Column

Subsequently to the virus inactivation, pH adjustment and filtration the conditioned virus inactivation pool was processed over a Capto Q column in FT mode in two cycles. The method comprises the cleaning in place step 1 (buffer 0.5 M NaOH), an equilibration step (20 mM Na-citrate, pH 5), a load step of conditioned virus inactivation solution, a washing step (20 mM Na-citrate, pH 5.0), a regeneration step (20 mM Na-citrate, 1 M Na-Cl, pH 5.5), a cleaning in place step 2 (0.5 M NaOH) and a storage step (0.01 M NaOH).

The UV280 profiles of the two cycles are congruent and show the expected increase of the UV280 absorption profile during application of the conditioned Protein A eluate.

Figure 4A:
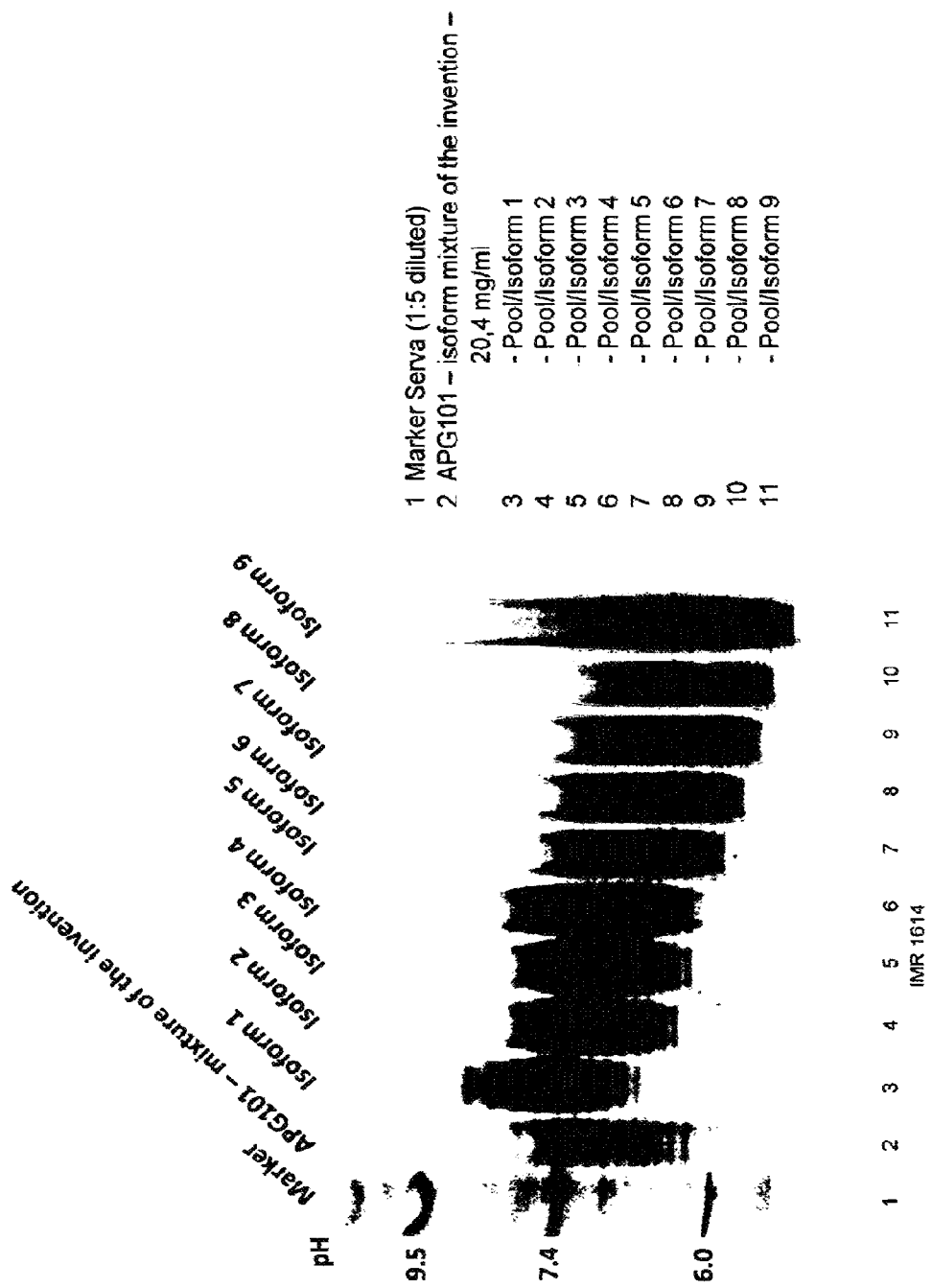
FIG. 4a: IEF of AEX fraction of an APG101 mixture obtained by the inventive method.

Each obtained flow through fraction was finally 0.22 μm filtered (Sartobran P) in order to address bioburden reduction. Afterwards, the separate fractions were pooled and stored at 21±3° C. until further processing via the MMC step (C30). A comparison of AIEX fractions of a mixture of APG101 isoforms obtained by the inventive method and of APG101 obtained by a non-inventive method by IEF is shown in FIGS. 4a and 4b.

The yields of the AIEX runs were around 100%.

2.4 MMC (C30)—Column

After the C20 step the AIEX product pool was processed over a Capto MMC column in three cycles. The method comprised a cleaning in place step (buffer 0.5 M NaOH), an equilibration step (20 mM Na-citrate, pH 5.0), a load step using the AIEX product/wash, a wash step (20 mM Na-citrate, pH 5.0), an elution step (50 mM Na-phosphate, 105 mM NaCl, pH 7.4), a regeneration step (3 M NaCl, pH 11), a cleaning in place step (0.5 M NaOH), a conditioning step (50 mM Na-phosphate, 105 mM NaCl, pH 7.4) and a storage step (20 mM Na-phosphate, 20% ethanol, pH 7.5).

The elution was induced via an increase of the pH. The UV280 profiles of the three cycles are highly congruent and show the expected shape including the typical single peak within the elution step.

Subsequently, the eluate fractions were each filtered over a 0.22 μm filter (Sartobran P) and stored at 21±3° C. Prior to further processing via the virus filtration step the particular Capto MMC eluate fractions were pooled.

The yields of the MMC runs range around 100%.

2.5 Virus Filtration (I10)

Subsequent to the C30 step the Capto MMC eluate pool (1181 mL) was passed over a Durapore 0.1 μm filter (Millipak 20) prior to the virus filtration. The virus filtration was executed applying an aliquot of the 0.1 μm filtrate (887 mL) on a Planova 15N virus filter (100 cm2) equilibrated with 50 mM PBS, pH 7.4 (Capto MMC elution buffer) at a working pressure of 0.8±0.1 bar. The post-wash volume was 0.5 mL/cm2 using equilibration buffer. Filter testing was done prior to filter usage based on detection of pressurized air bubbling. The filtrate flux remained constant during processing (ca. 22 L/m2*h).

The virus filtration resulted in 99% yield.

Subsequently, the residual 0.1 μm filtrate and the filtrate fraction of the virus filtration was pooled and stored at 5±3° C. until further processing via subsequent UF/DF step.

2.6 Ultrafiltration/Diafiltration (I20)

Prior to diafiltration the I10 filtrate was concentrated on an ÄKTA Crossflow system to a protein concentration of 25.0±2.0 mgAPG101/mL using two Pellicon 3 30 kDa cassettes. Afterwards, a diafiltration was executed to change the buffer system to the following buffer:

50 mM Na-Phosphate, 5% Sorbitol, pH 6.5

The material was ultrafiltrated to the above mentioned concentration and diafiltrated by factor 7.0±0.5. The parameters for the ultra- and diafiltration were:
Retentate flow: 450 L/(m2*h)
TMP: 1.2±0.1 bar
The UF/DF yielded in 97% product recovery.

2.7 Drug Substance Concentration Adjustment

For final concentration adjustment a defined volume (107 mL) of the formulation buffer (50 mM Na-Phosphate, 5% Sorbitol, pH 6.5) was added to the UF/DF retentate pool. The final drug substance concentration obtained by A280 was 20.4 mg/mL. Finally, the drug substance was 0.22 µm filtered (Sartobran P). Subsequently, aliquots of the drug substance with a volume of 200 µL were bottled in 500 µL vials.

2.8 Total Yield

The step and total yields obtained from ProA-HPLC and A280 analysis are listed in Table 1. The sampling of the target molecule was not taken into account for the calculation of the yields.

TABLE 1

Overview of step yield

| Sample | Total yield (%) | |
|---|---|---|
| Protein A capture (C10) | 96[#1] | 101[#2] |
| Virus inactivation (V10) | 90 | 94 |
| AIEX (C20) | 90 | 94 |
| MMC (C30) | 90 | 94 |
| Virus filtration (I10) | 89 | 93 |
| UF/DF (I20) | 86 | 90 |
| Formulation (I30) | 86 | 90 |

[#1]Load determined via ProA-HPLC harvest method, Eluate via ProA-HPLC.
[#2]Load determined via ProA-HPLC harvest method, Eluate via A280.

The identity of the mixture of APG101 isoforms was confirmed via non-reducing SDS Page and IEF. The isoform pattern showed additional basic bands compared to the reference material and a slight shift in the isoform distribution towards acidic pI.

This is shown, for example, by a comparison of an IEF gel of AX fractions obtained by the method of the present invention and an APG101 mixture obtained by the non-inventive method according to FIG. 1.

The APG101 isoform mixture of the present invention further differs in the presence of carbohydrates (N-glycans sialic acid).

Carbohydrates (Antennarity/N-glycans)

In Table 2 the analysis of the carbohydrate structure is summarized. Despite a comparable carbohydrate structure between the reference material and the inventive composition the distribution of carbohydrate structures differs.

TABLE 2

N-glycans (carbohydrates) analysis result

| Peak/Sample | Reference material (Mol-%) | Inventive composition (Mol-%) |
|---|---|---|
| cF1GN2 | 34.1 | 18.2 |
| cF1GN2G1 | 19.2 | 17.8 |
| cF1GN2G3 | 30.1 | 51.5 |
| cF1GN2G3 | 9.1 | 7.6 |
| Other | 7.6 | 4.9 |

Carbohydrates (Sialic Acids)

The analysis of the amount of sialic acid per mol of APG101 of the inventive composition is summarized in Table 3.

TABLE 3

Sialic acid (carbohydrate) analysis

| Sample | Sialic acid content (mol NeuAc/mol APG101) |
|---|---|
| Inventive composition | 5.1 |
| Reference material | 3.9 |

The reference material always relates to an APG101 mixture which was not produced by the method of the present invention.

Finally, an assay was carried out to measure the bioactivity of the mixture according to the present invention comprising APG101 isoforms.

3. Method for the Determination of the In Vitro Potency of APG101 Isoforms

Figure 5:
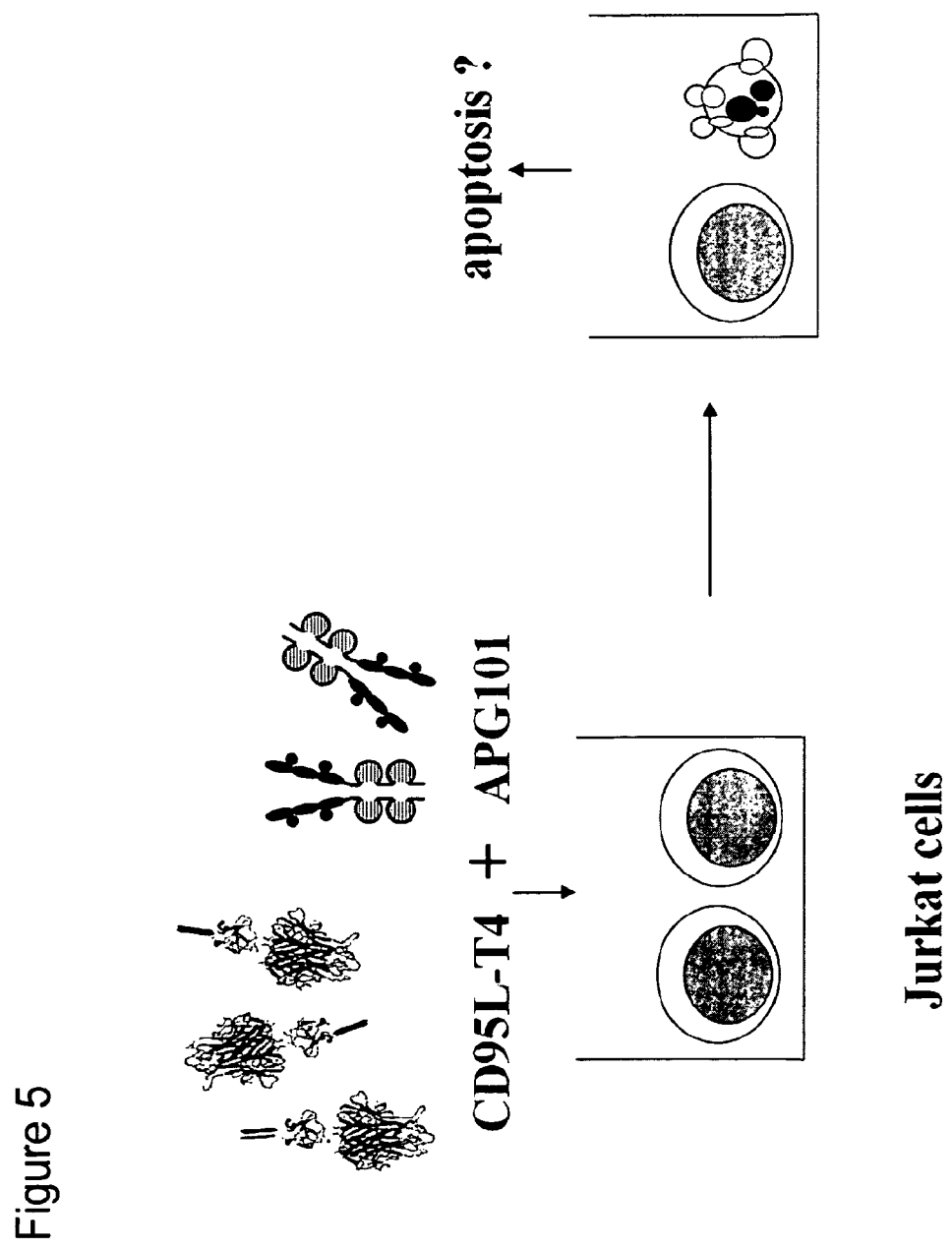
FIG. 5: Schematic overview of the potency assay.

A cellular assay with a Jurkat A3 permanent T-cell line is used for the determination of biological activity of the APG101. This potency is schematically shown in FIG. 5.

With this apoptosis assay employing Jurkat A3 cells, EC50 values for the inhibition of APG293 (=CD95L-T4; 250 ng/ml) induced apoptosis by APG101 are determined.

In brief, Jurkat A3 cells are grown in flasks with RPMI 1640-medium+GlutaMAX (GibCo) supplemented with 10% FBS, 100 units/ml Penicillin and 100 µg/ml Streptomycin. 100,000 cells are seeded per well into a 96-well microtiter plate. CD95L-T4 (APG293) at a constant concentration of 250 ng/ml is incubated in a separate 96-well microtiter plate for 30 minutes at 37° C. with different concentrations of APG101. The addition of the APG101/CD95L-T4 mixture to the cells is followed by 3 hours incubation at 37° C. Cells are lysed by adding lysis buffer (250 mM HEPES, 50 mM MgCl2, 10 mM EGTA, 5% Triton-X-100, 100 mM DTT, 10 mM AEBSF, pH 7.5) and plates are put on ice for 30 minutes to 2 hours. Apoptosis is paralleled by an increased activity of Caspases (e.g. caspases 3 and 7). Hence, cleavage of the Caspase substrate Ac-DEVD-AFC is used to determine the extent of apoptosis. In fact, caspase activity correlates with the percentage of apoptotic cells determined morphologically after staining the cells with propidium iodide and Hoechst-33342.

For the caspase activity assay, 20 µl cell lysate is transferred to a black 96-well microtiter plate. After the addition of 80 µl buffer containing 50 mM HEPES, 1% Sucrose, 0.1% CHAPS, 50 µM Ac-DEVD-AFC, and 25 mM DTT, pH 7.5, the plate is transferred to a Tecan microtiter plate reader and the increase in fluorescence intensity over a given time frame is monitored (excitation wavelength 400 nm, emission wavelength 505 nm). Employing the GraphPad Prism software, EC50 values for APG101 (i.e. reduction of apoptosis induction of the given concentration of CD95L by 50%) are calculated.

Determination of the biological activity of APG101 employing the potency assay enables:
- a high specificity. Via its interaction with CD95, CD95L-T4 induces apoptosis on Jurkat A3 cells. The CD95/CD95L-T4 interaction is specifically blocked by the addition of APG101.
- the use of a relevant cellular system; induction of apoptosis is one important physiological feature of the CD95/CD95L signaling and can be monitored in the well characterized human T-cell line Jurkat A3.
- a high sample throughput due to the application of 96 well microtiter plates and short incubation times.

Figure 6:
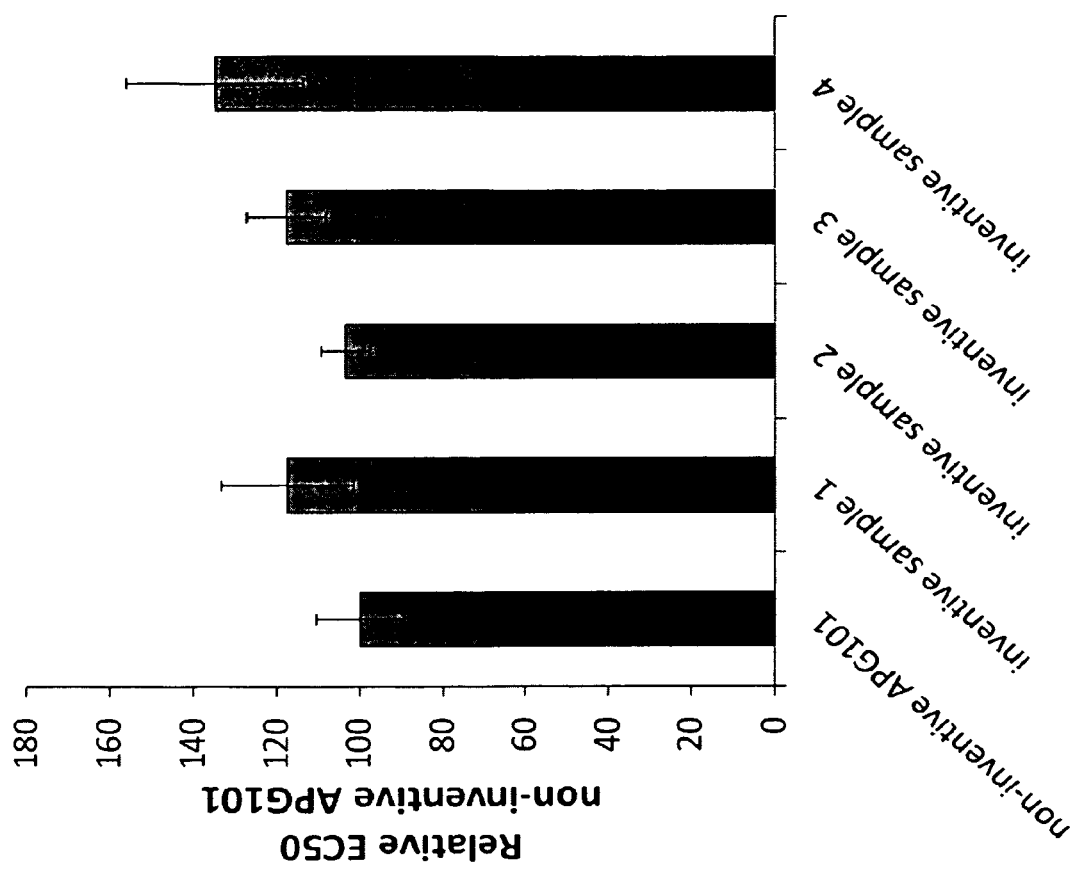
FIG. 6: In vitro biological activity (EC50) of APG101 isoform mixtures obtained by the inventive method compared with APG101 obtained by non-inventive methods.

FIG. 6 shows the biological activity (EC50) of APG101 isoforms mixtures obtained by the inactive method (inventive samples) compared to APG101 obtained by non-inventive methods. The activity is comparable.

EXAMPLE 2

Background:

Environmentally-sensitive dyes, such as Sypro Orange, have been applied to the detection of protein unfolding in thermal shift assays, by a procedure referred to as the Thermofluor technique. In the procedure, dyes interact with exposed hydrophobic regions generated by partial or full unfolding of proteins.

Method Procedure:

The investigated proteins and Sypro Orange were pipetted to Flat Cap Strips (BioRad, cat. no. TCS0803) in a 48-well plate (low white, BioRad, cat. no. MLL4851). In a final volume of 25 µl the concentration of the investigated proteins was 500 µg/ml (diluted with PBS, pH 7.4) and 1:1000 for Sypro Orange (Invitrogen, cat. no. S6650). The cycler (BioRad MiniOpticon) was run as follows: 2 minutes at 25° C., then plate read; from 25° C. to 95° C. an increment of 1° C. every 10 seconds with a plate read after each 1° C. increment.

Figure 8:
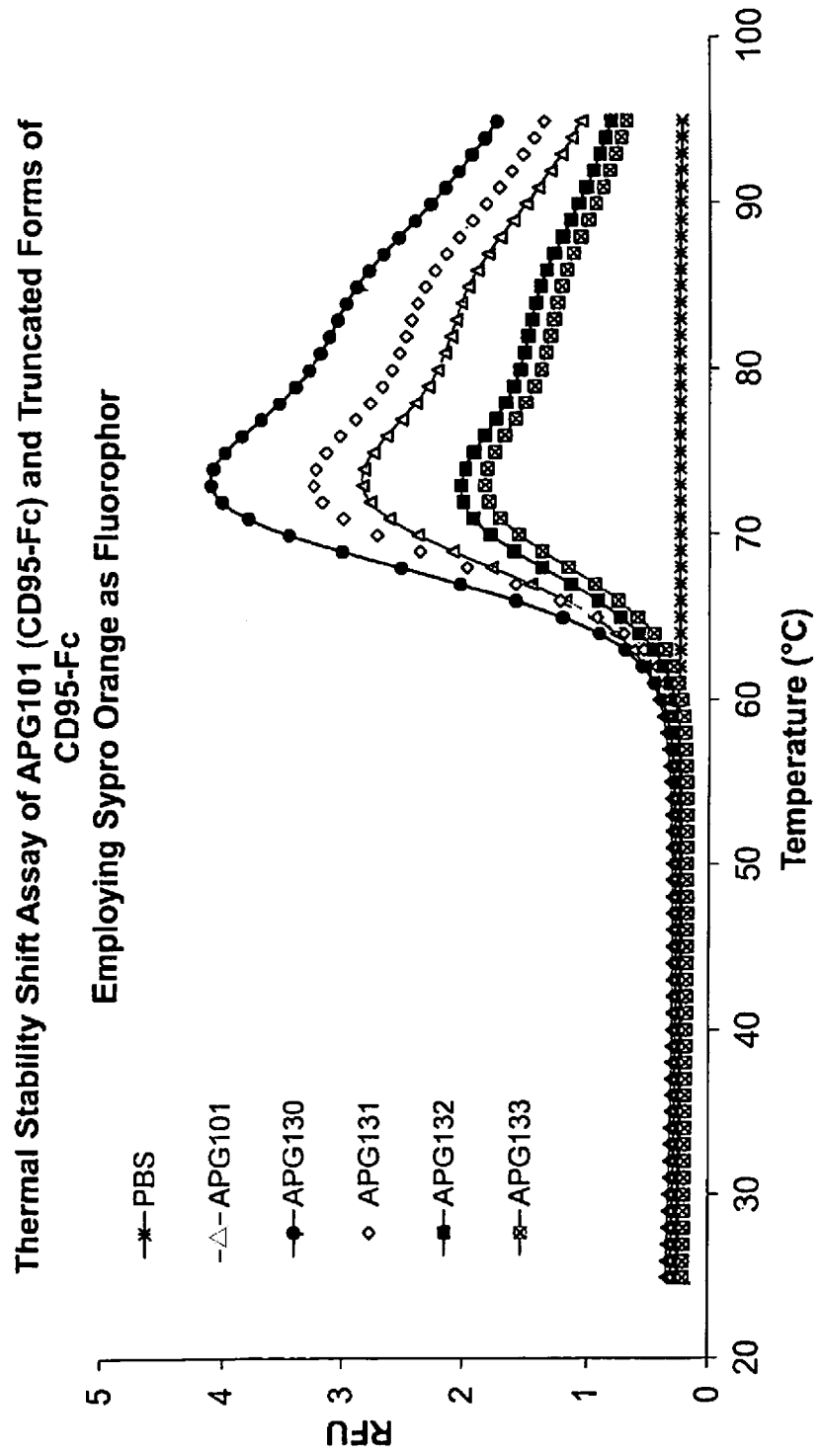
FIG. 8: Thermal stability shift assay of APG101 (CD95-Fc) and mature, i.e. truncated forms of CD95-Fc (APG130, APG131, APG132 and APG133) employing Sypro Orange as fluorophor. Sypro Orange was used as a 1:1000 dilution. Melting points of the proteins were calculated and are displayed in Table 4.

Results:

As can be seen in FIG. 8, the truncated form of CD95-Fc (APG101) have the same stability compared with CD95-Fc as expressed by essentially the same melting point Tm (Table 4).

TABLE 4

Melting points (Tm) of APG101 (CD95-Fc) and truncated forms of APG101 (APG130, APG131, APG132 and APG133). The respective thermal stability shift assay curves employing Sypro Orange as fluorophor are displayed in FIG. 8.

|  | APG101 | APG130 | APG131 | APG132 | APG133 |
|---|---|---|---|---|---|
| Tm (° C.) | 69 | 68 | 69 | 68 | 68 |

The invention claimed is:

1. An artificial signal peptide consisting of SEQ ID NO:2.
2. A polypeptide comprising the signal peptide of claim 1.
3. The polypeptide of claim 2, comprising a mature peptide starting with lysine, threonine, aspartic acid or glutamine.
4. An artificial signal peptide consisting of a sequence having at least 95% identity to SEQ ID NO:2.
5. A polypeptide comprising the signal peptide of claim 4.
6. The polypeptide of claim 5, comprising a mature peptide starting with lysine, threonine, aspartic acid or glutamine.

* * * * *